(12) United States Patent
van Hal et al.

(10) Patent No.: US 10,359,412 B2
(45) Date of Patent: Jul. 23, 2019

(54) SYSTEMS AND METHODS FOR DETECTION OF MERCURY IN HYDROCARBON-CONTAINING FLUIDS USING OPTICAL ANALYSIS OF SLUG FLOW

(71) Applicant: SCHLUMBERGER TECHNOLOGY CORPORATION, Sugar Land, TX (US)

(72) Inventors: Ronald E. G. van Hal, Cambridge, MA (US); Vincent Sieben, Cambridge, MA (US); Cedric Floquet, Cambridge, MA (US); Victoria Lee, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 46 days.

(21) Appl. No.: 15/254,925

(22) Filed: Sep. 1, 2016

(65) Prior Publication Data
US 2018/0059088 A1    Mar. 1, 2018

(51) Int. Cl.
*G01N 15/06*    (2006.01)
*G01N 33/28*    (2006.01)

(52) U.S. Cl.
CPC ......... *G01N 33/2858* (2013.01); *G01N 15/06* (2013.01); *G01N 2015/0675* (2013.01); *G01N 2015/0693* (2013.01)

(58) Field of Classification Search
CPC ............... G01N 33/2858; G01N 15/06; G01N 2015/0693; G01N 2015/0675;
(Continued)

(56) References Cited

U.S. PATENT DOCUMENTS

| 4,860,581 A | 8/1989 | Zimmerman et al. |
| 6,058,773 A | 5/2000 | Zimmerman et al. |

(Continued)

FOREIGN PATENT DOCUMENTS

WO    WO2009077183 A1    6/2009

OTHER PUBLICATIONS

Clevenger, W. L. et al., "Trace Determination of Mercury: A Review", Critical Reviews in Analytical Chemistry, 27 (1), 1997, pp. 1-26.
(Continued)

*Primary Examiner* — Lore R Jarrett

(57) ABSTRACT

A method and system for detecting mercury in a hydrocarbon-containing fluid stores a sample of the hydrocarbon-containing fluid in a first reservoir. A liquid phase reagent solution is stored in a second reservoir. The liquid phase reagent solution includes nanoparticles with an affinity to mercury, wherein the nanoparticles are suspended as a colloid in the liquid phase reagent solution. The sample of the hydrocarbon-containing fluid is delivered from the first reservoir into a first port of a fluidic device while the liquid phase reagent solution is delivered from the second reservoir into a second port of the fluidic device such that the fluidic device produces slug flow. The slug flow is subject to optical analysis that determines concentration of mercury in the sample of the hydrocarbon-containing fluid.

32 Claims, 15 Drawing Sheets

(58) Field of Classification Search
CPC .. G01N 33/2835; G01N 21/82; G01N 1/4055; G01N 21/31; G01N 1/28; G01N 33/24; G01N 33/42; G01N 33/2823; G01N 2201/12; G01N 2001/4061; G01N 2001/381; G01N 33/1813; G01N 33/0045; G01N 27/26; G01N 21/554; G01N 2201/088; G01V 3/32; B01F 5/0647; B01F 13/0059; B01L 3/5027; B01L 2300/0883; B01L 2300/0681; B01L 2300/0867; B01L 2300/0636; B01L 2300/0627; E21B 49/081; E21B 43/00; G01J 3/42; G01J 2003/425
See application file for complete search history.

(56) References Cited

U.S. PATENT DOCUMENTS

| | | | |
|---|---|---|---|
| 7,534,560 | B2 | 5/2009 | Lu et al. |
| 7,612,185 | B2 | 11/2009 | Lu et al. |
| 7,892,734 | B2 | 2/2011 | Lu et al. |
| 8,062,893 | B2 | 11/2011 | Wang et al. |
| 8,470,532 | B2 | 6/2013 | Lu et al. |
| 8,826,981 | B2 | 9/2014 | van Hal et al. |
| 9,291,557 | B2 | 3/2016 | James et al. |
| 2008/0066535 | A1* | 3/2008 | Vasques ............... E21B 33/1246 73/152.17 |
| 2010/0253933 | A1 | 10/2010 | Guieze et al. |
| 2011/0174688 | A1 | 7/2011 | Milam et al. |
| 2012/0212733 | A1* | 8/2012 | Kodali ................... B82Y 15/00 356/301 |
| 2013/0071934 | A1* | 3/2013 | Indo ........................ G01N 21/80 436/28 |
| 2014/0034320 | A1* | 2/2014 | Ladva ..................... C09K 8/035 166/305.1 |
| 2014/0078499 | A1 | 3/2014 | Tunheim et al. |
| 2014/0333933 | A1* | 11/2014 | James ................ G01N 33/0045 356/432 |
| 2014/0371105 | A1 | 12/2014 | Thomas et al. |
| 2015/0112102 | A1 | 4/2015 | Jensen |
| 2016/0115787 | A1 | 4/2016 | Mostowfi et al. |
| 2017/0159430 | A1 | 6/2017 | van Hal et al. |

OTHER PUBLICATIONS

McNerney, J. J. et al., "Mercury Detection by Means of Thin Gold Films", Science, 1972, 178(4061), pp. 611-612.

Mirsky, V. M. et al., "Chemical sensors for mercury vapour", Chapter 12 in Comprehensive Analytical Chemistry, 2007, 49, pp. 235-251.

Chansuvarn, W. et al., "Visual and colorimetric detection of mercury(II) ion using gold nanoparticles stabilized with a dithia-diaza ligand", Microchim Acta, 2012, 176, pp. 57-64.

Scallan, K. et al., "Optical Characterization of the Interaction of Mercury with Nanoparticulate Gold Suspended in Solution", in Sensors and Transducers, 2007, 85(11), pp. 1667-1698.

Chen, L. et al., "Colorimetric Detection of Mercury Species Based on Functionalized Gold Nanoparticles", ACS Applied Materials & Interfaces, 2014, 6(18), pp. 15897-15904.

Du, J. et al., "Colorimetric Detection of Mercury Ions Based on Plasmonic Nanoparticles" Small, 2013, 9(9-10), pp. 1467-1481.

Crosby, J. S. et al., "Determination of total mercury concentration in aqueous samples with nanoparticles", Analytical Methods, 2014, 6(4), pp. 1254-1260.

Zhengquan, Y. et al., "Advances for the colorimetric detection of Hg2+ in aqueous solution", RSC Advances, 2014, 4, pp. 48373-48388.

Lin, C. Y. et al., "Colorimetric Sensing of Silver(I) and Mercury(II) Ions Based on an Assembly of Tween 20-Stabilized Gold Nanoparticles", Analytical Chemistry, 2010, 82(16), pp. 6830-6837.

Zhao, C.-X. et al., "Two-phase microfluidic flows", Chemical Engineering Science, 2011, 66(7), pp. 1394-1411.

Burns, J. R. et al., "The intensification of rapid reactions in multiphase systems using slug flow in capillaries", Lab on a Chip, 2001, 1(1), pp. 10-15.

Kashid, M.N. et al., "Internal Circulation within the Liquid Slugs of a Liquid-Liquid Slug-Flow Capillary Microreactor", Industrial & Engineering Chemistry Research, 2005. 44(14), pp. 5003-5010.

Matsuyama, K. et al., "Operation of microfluidic liquid slug formation and slug design for kinetics measurement", Chemical Engineering Science, 2007, 62(18-20), pp. 5133-5136.

Kretschmann, E. et al., "Radiative Decay of Non Radiative Surface Plasmons Excited by Light", Zeitschrift fur Naturforschung A, 1968, 23a, pp. 2135-2136.

Smythe, E. et al., "Optical properties of surface plasmon resonances of coupled metallic nanorods", Optics Express, 2007, 15(12), pp. 7439-7447.

Boulart, C. et al., "Sensing Dissolved Methane in Aquatic Environments: An Experiment in the Central Baltic Sea Using Surface Plasmon Resonance", Environmental Science & Technology, 2013, 47(15), pp. 8582-8590.

Mulvaney, P., "Surface Plasmon Spectroscopy of Nanosized Metal Particles", Langmuir, 1996, 12(3), pp. 788-800.

Jorgenson, R. C. et al., "A fiber-optic chemical sensor based on surface plasmon resonance", Sensors and Actuators B: Chemical, 1993, 12(3), pp. 213-220.

Search Report and Written Opinion of International Patent Application No. PCT/US2017/049796 dated Dec. 8, 2017, 19 pages.

* cited by examiner

SYSTEMS AND METHODS FOR DETECTION OF MERCURY IN HYDROCARBON-CONTAINING FLUIDS USING OPTICAL ANALYSIS OF SLUG FLOW

FIELD

The present application relates to methods, apparatus and systems that measure the mercury content in hydrocarbon-containing fluids.

BACKGROUND

Elemental mercury is frequently present in hydrocarbon reservoirs and due to its physical properties and vapor pressure, it is produced in the natural gas phase. Mercury vapor is heavy and the production mechanisms in the reservoir are not completely understood, but some hypotheses mention that it could be produced as puffs or slugs, which could explain the variation between samples.

The presence of mercury in natural gas presents serious health and safety issues. It attacks the central nervous system of humans and accumulates in the liver and kidneys. Mercury can also generate amalgams with common metals; including but not limited to: aluminum, copper, silver and gold. Mercury is under suspicion of causing stress cracking in titanium alloys resulting in catastrophic failure of vessels. Mercury can cause metal embrittlement leading to serious problems in refineries. Therefore, producers, transporters, and distributors of oil and natural gas wish to better monitor the mercury content in such hydrocarbon fluids.

SUMMARY

In accordance with some examples, methods and systems for detecting mercury in a hydrocarbon-containing fluid are provided that store a sample of the hydrocarbon-containing fluid in a first reservoir. A liquid phase reagent solution is stored in a second reservoir. The liquid phase reagent solution includes nanoparticles with an affinity to mercury, wherein the nanoparticles are suspended as a colloid in the liquid phase reagent solution. The sample of the hydrocarbon-containing fluid is delivered from the first reservoir into a first port of a fluidic device while the liquid phase reagent solution is delivered from the second reservoir into a second port of the fluidic device such that the fluidic device produces slug flow. The fluidic device can employ flow channels that range from 1-5000 microns. The slug flow is subject to optical analysis that determines concentration of mercury in the sample of the hydrocarbon-containing fluid.

In one or more embodiments, the slug flow produced by the fluidic device can include a liquid phase that carries amalgam nanoparticles that are suspended as a colloid in the liquid phase of the slug flow. The amalgam nanoparticles are an alloy of mercury with another metal. The slug flow produced by the fluidic device can be controlled by the flow rate of the hydrocarbon-containing fluid sample and the flow rate of the liquid phase reagent solution supplied to the fluidic device.

In one or more embodiments, a first pump can be configured to pump the sample of hydrocarbon-containing fluid from the first reservoir to the first input port of the fluidic device, and a second pump can be configured to pump the liquid phase reagent solution from the second reservoir to the second input port of the fluidic device.

In one or more embodiments, the liquid phase reagent solution can include water and water-soluble polymer (such as poly(acrylic acid)) that stabilizes the suspension of the nanoparticles in the liquid phase reagent solution at high temperature conditions.

In one or more embodiments, the nanoparticles can be formed from a noble metal, a silica core coated with a noble metal (e.g., gold) shell, a noble metal (e.g., gold) core coated with a silica shell, or recursive layers of silica and a noble metal (e.g., gold) possibly with varying thickness. Such nanoparticles can be designed and/or selected to have a particular SPR wavelength, which shifts due to accumulation of mercury thereon as described herein. The nanoparticles can have a concentration of up to $1 \times 10^{15}$ nanoparticles/cm$^3$ in the liquid phase reagent solution.

In one or more embodiments, the flow rate of the hydrocarbon-containing fluid sample and the flow rate of the liquid phase reagent solution supplied to the fluidic device can be controlled according to fluid analysis that determines the appropriate class of fluid sample type and pump control settings that dictate the flow rate of the hydrocarbon-containing fluid sample and the flow rate of the liquid phase reagent solution for producing the desired slug flow.

In one or more embodiments, the fluidic device can include a mixer section upstream from a reactor section, wherein the mixer section produces the slug flow from the hydrocarbon-containing fluid sample and the liquid phase reagent solution introduced into the first and second input ports, and wherein the reactor section extracts mercury of hydrocarbon-containing fluid sample where it adsorbs on the nanoparticles to form the amalgam nanoparticles contained in the slug flow.

In one or more embodiments, the optical analyzer can include a flow-thru optical cell, a light source and a detector. The light source and the detector can be configured to perform absorption spectroscopy. The detector can measure the transmission spectrum of light for the slug flow passing through the flow-thru optical cell. The optical analyzer can further include a data processing system that processes the transmission spectrum to determine a shift in SPR peak wavelength and uses the shift in SPR peak wavelength to determine mercury concentration in the hydrocarbon-containing fluid sample.

In one or more embodiments, the hydrocarbon-containing fluid sample can be selected from: a gas phase fluid sample that includes gaseous hydrocarbons, a liquid phase fluid sample that includes oil, and a gas and liquid phase fluid sample including a mixture of gaseous hydrocarbons and oil.

In one or more embodiments, the mercury detection system can be part of a downhole tool to determine mercury concentration in a sample of formation fluid collected by the downhole tool.

In one or more embodiments, the mercury detection system can be part of a surface-located facility to determine mercury concentration in fluids produced from a production well.

DETAILED DESCRIPTION OF THE PREFERRED EMBODIMENTS

Figure 1A:
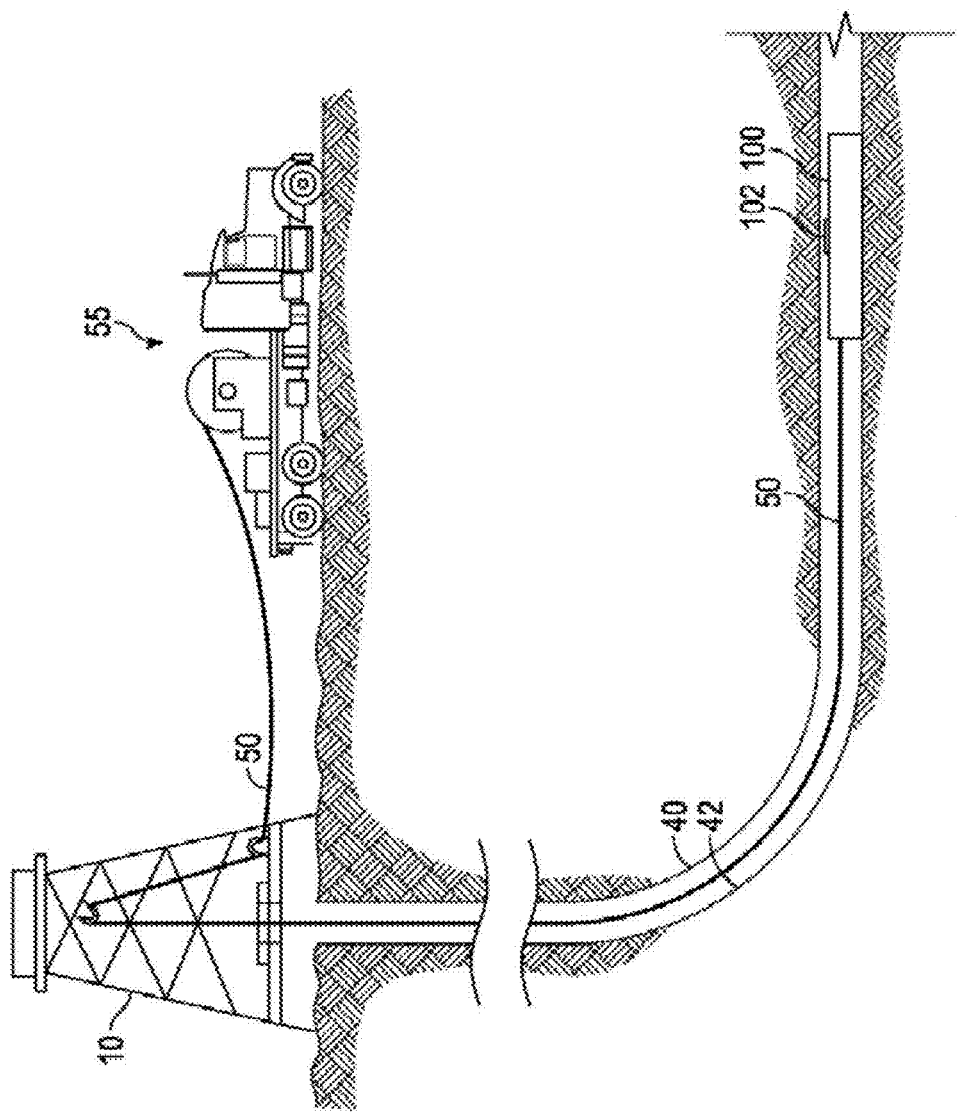
FIG. 1A is a schematic diagram showing one example of a rig on which disclosed downhole tool embodiments may be utilized.

Before example embodiments of the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The term "nanoparticles" as used herein means particles that have an average size in the nanometer size range, such as an average size ranging from 1 nm to 1000 nm. By "average size" is meant the statistical mean average size. For example, nanoparticles of the present disclosure may have an average size ranging from 1 nm to 1000 nm, including from 1 nm to 750 nm, or from 1 nm to 500 nm, or from 1 nm to 250 nm, or from 1 nm to 100 nm, such as from 10 nm to 75 nm. In some instances, the nanoparticles may have a smaller average size ranging from 1 nm to 100 nm, or 1 nm to 75 nm, such as from 1 nm to 50 nm, including from 1 nm to 25 nm, or from 1 nm to 10 nm, or from 1 nm to 5 nm, or from 3 nm to 5 nm. In certain embodiments, the nanoparticles are substantially free of a surface coating. Nanoparticles that are substantially free of a surface coating are configured such that the exterior surface of the material of the nanoparticle is directly exposed to the surrounding environment. For example, the nanoparticles may be washed to remove any surface coating present on the material of the nanoparticles.

The term "slug" or "slugs" or "slug flow" as used herein refers to a multiphase (gas-liquid) flow regime in a flow channel in which most of the lighter gas phase is contained in large bubbles dispersed within, and pushing along, the heavier liquid phase. The heavier liquid phase is generally continuous along the wall(s) of the flow channel. The slug normally refers to the heavier liquid phase, but sometimes to the bubbles of lighter gas phase. There may also be smaller gas phase bubbles within the liquid phase, but many of these have coalesced to form the large gas phase bubbles until they span much of the flow channel.

The term "fluidic device" as used herein refers to a device or apparatus that deals with manipulation of fluids that are constrained to small-sized flow channels whose maximal cross-sectional dimension is up to 5 millimeters. A microfluidic device is a kind of fluidic device with sub-millimeter scale flow channels whose maximal cross-sectional dimension is less than 1 millimeter. The microfluidic device can include a planar substrate (such as glass) with the sub-millimeter scale flow channels etched into the planar substrate. The microfluidic device can include a network of these embedded channels that transport the sample from one operation to the next. The microfluidic device allows for manipulation of small volumes of fluid to provide precise control of reagents and seamless automation of several consecutive steps.

The term "surface plasmon resonance" or "SPR" as used herein is the resonant oscillation of conduction electrons at the interface between a negative and positive permittivity material stimulated by incident light. The resonance condition is established at an SPR peak wavelength where the frequency of incident photons matches the natural frequency of surface electrons oscillating against the restoring force of positive nuclei and thus local maximum in absorbance occurs.

Systems

Systems of some examples of the present disclosure are configured to make determinations of the concentration of mercury in a hydrocarbon-containing fluid sample. In some embodiments, the system can include a fluidic device (such as microfluidic device) and optical analyzer. The fluidic device can be configured to form a gas-liquid or liquid-liquid slug flow from a liquid phase reagent solution and a hydrocarbon-containing fluid sample supplied to the fluidic device. The liquid phase reagent solution includes nanoparticles suspended in the liquid phase reagent solution. The nanoparticles of the liquid phase reagent solution of the slug flow can adsorb mercury of the hydrocarbon-containing fluid sample that is contained in the slug flow to form the amalgam nanoparticles contained in the slug flow. The amalgam nanoparticles are an alloy of mercury with another metal. The optical analyzer can include a flow-thru optical cell that defines a flow line that carries the slug flow produced by the fluidic device for optical analysis. The flow-thru optical cell can be realized from a material that is substantially transparent (such as, but not limited to, glass, quartz, and the like) such that light is transmitted through the material.

In some embodiments, the liquid phase reagent solution can include water and a water soluble polymer additive that stabilizes the suspension of the nanoparticles in the liquid phase reagent solution at high temperature downhole conditions. For example, the polymer additive can be poly (acrylic acid), poly(acrylamide-co-acrylic acid), poly(vinyl pyridine), poly(ethylene oxide), poly(vinyl alcohol), poly(4-styrene sulfonic acid), a poly (methacrylic acid), poly (vinyl pyrrolidone) and the like.

In some embodiments, the nanoparticles of the liquid phase reagent solution can be made of a material that adsorbs mercury. For instance, the nanoparticles may be made of a noble metal, such as silver or gold or copper or be an oxide, such as zinc oxide and indium tin oxide or an oxide coated noble metal such as zinc oxide coated gold that adsorbs mercury.

In some embodiments, the nanoparticles can be formed from a silica core coated with a noble metal (e.g., gold) shell, a noble metal (e.g., gold) core coated with a silica shell, or recursive layers of silica and a noble metal (e.g., gold) possibly with varying thickness. Such nanoparticles can be designed and/or selected to have a particular SPR wavelength, which shifts due to accumulation of mercury thereon as described herein.

In some embodiments, the nanoparticles can have a concentration up to $1 \times 10^{15}$ nanoparticles/cm$^3$ in the liquid phase reagent solution.

In some embodiments, the slug flow produced by the fluidic device includes a liquid phase that carries amalgam nanoparticles that are suspended as a colloid in the liquid phase of the slug flow.

In some embodiments, the slug flow produced in the fluidic device can be controlled by the flow rate of the hydrocarbon-containing fluid sample and the flow rate of the liquid phase reagent solution supplied to the fluidic device. The slug flow can be influenced by certain properties (such as viscosity or surface tension) of hydrocarbon-containing fluid sample that can vary across samples. One or more of such properties can be measured by fluid analysis and the property measurements input to a classifier engine that determines the appropriate class of fluid sample type and the pump control settings that dictate the flow rate of the hydrocarbon-containing fluid sample and the flow rate of the liquid phase reagent solution for producing the desired slug flow.

In some embodiments, the optical analyzer can include a light source. The light source may be configured to direct light from the light source to the flow-thru optical cell for optical analysis of the slug flow passing through the optical cell. In certain embodiments, the light source is a visible light source. The visible light source may be configured to emit light in the visible range of the electromagnetic spectrum. In other embodiments, the light source may be configured to emit light in the ultraviolet (UV) range, or the infrared range of the spectrum. In embodiments of the light source configured to emit light on the visible range of the spectrum, the light source may include, but is not limited to, a lamp (e.g., a halogen lamp), LEDs (Light Emitting Diodes), a laser, and the like.

In some embodiments, the optical analyzer can include a detector. In some instances, the detector is a light detector. The light detector may be configured to detect light passing through the flow-thru optical cell for optical analysis of slug flow passing through the optical cell. In some cases, the detector can be configured to detect light in the visible range of the electromagnetic spectrum. In other cases, the detector can be configured to detect light in the infrared range of the electromagnetic spectrum. In yet other cases, the detector can be configured to detect light in the ultraviolet range of the electromagnetic spectrum. In still other cases, the detector can be configured to detect light in more than one range of the electromagnetic spectrum, such as in the ultraviolet and visible, or the visible and infrared, or the ultraviolet, visible and infrared ranges of the spectrum. In certain embodiments, the detector can be a spectrometer, a bolometer for infrared detection, mercury cadmium telluride and other cooled semiconductor detectors for infrared detection, photodiodes and photomultiplier tubes for visible and ultraviolet detection, and the like.

In some embodiments, the optical analyzer can include a light source and detector that are configured to perform absorption spectroscopy. In this configuration, the light source generates light. The detector measures an incident light spectrum of the light generated by the light source and then re-measures the sample spectrum after placing the sample of interest between the light source and detector. The two measured spectra can then be combined to determine the transmission spectrum of the sample of interest. In certain embodiments, the detector can be configured to measure the transmission spectrum of light for slug flow passing through the optical cell. The optical analyzer can also include a data processing system that processes the transmission spectrum to determine a shift in SPR peak wavelength. The adsorption of mercury onto nanoparticles can form amalgam nanoparticles that are suspended as a colloid in the liquid phase of the slug flow. The formation of such amalgam nanoparticles may cause the SPR peak wavelength to shift from its original wavelength (e.g., the SPR peak wavelength in the absence of mercury). As such, the shift in the SPR peak wavelength may indicate the presence of mercury in the slug flow. For instance, the shift in the SPR peak wavelength may be proportional to the mass fraction of mercury adsorbed by nanoparticles to form the amalgam nanoparticles, and thus can be used as the basis of quantification of mercury concentration in the slug flow and thus the mercury concentration in the hydrocarbon-containing fluid sample that forms the slug flow.

In some embodiments, the system can be configured to determine the concentration of mercury in a hydrocarbon-containing fluid sample at concentrations of 1 μg/m$^3$ to 1 g/m$^3$.

Methods

Aspects of some example embodiments of the present disclosure include methods that determine the concentration of mercury in a hydrocarbon-containing fluid sample. The methods include supplying a liquid phase reagent solution and a hydrocarbon-containing fluid sample to a fluidic device (such as microfluidic device) that forms a gas-liquid or liquid-liquid slug flow. The liquid phase reagent solution includes nanoparticles suspended in the liquid phase reagent solution. The nanoparticles of the liquid phase reagent solution of the slug flow can adsorb mercury of the hydrocarbon-containing fluid sample that is contained in the slug flow to form the amalgam nanoparticles contained in the slug flow. The method can further include flowing the slug flow through an optical analyzer for optical analysis that quantifies the mercury concentration in the slug flow and thus the mercury concentration of the hydrocarbon-containing fluid sample. The optical analyzer can include a flow-thru optical cell that defines a flow line that carries the slug flow produced by the fluidic device for the optical analysis. The flow-thru optical cell can be realized from a material that is substantially transparent (such as, but not limited to, glass, quartz, and the like) such that light is transmitted through the material.

In some embodiments, the liquid phase reagent solution can include water and a water-soluble polymer additive that stabilizes the suspension of the nanoparticles in the liquid phase reagent solution at high temperature downhole conditions. For example, the polymer additive can be poly (acrylic acid), poly(acrylamide-co-acrylic acid), poly(vinyl pyridine), poly(ethylene oxide), poly(vinyl alcohol), poly(4-styrene sulfonic acid), a poly (methacrylic acid), poly (vinyl pyrrolidone) and the like.

In some embodiments, the nanoparticles of the liquid phase reagent solution can be made of a material that adsorbs mercury. For instance, the nanoparticles may be made of a noble metal, such as silver or gold or copper or be an oxide, such as zinc oxide and indium tin oxide that adsorbs mercury.

In some embodiments, the nanoparticles can be formed from a silica core coated with a noble metal (e.g., gold) shell, a noble metal (e.g., gold) core coated with a silica shell, or recursive layers of silica and a noble metal (e.g., gold) possibly with varying thickness. Such nanoparticles can be designed and/or selected to have a particular SPR wavelength, which shifts due to accumulation of mercury thereon as described herein.

In some embodiments, the nanoparticles can have a concentration of up to $1 \times 10^{15}$ nanoparticles/cm$^3$ in the liquid phase reagent solution.

In some embodiments, the slug flow can include a liquid phase that carries amalgam nanoparticles that are suspended as a colloid in the liquid phase of the slug flow.

In some embodiments, the slug flow produced by the fluidic device can be controlled by the flow rate of the hydrocarbon-containing fluid sample and the flow rate of the liquid phase reagent solution supplied to the fluidic device. The slug flow can be influenced by certain properties (such as viscosity or surface tension) of hydrocarbon-containing fluid sample that can vary across samples. One or more of such properties can be measured by fluid analysis and the property measurements used as inputs to determine the appropriate class of fluid sample type and the pump control settings that dictate the flow rate of the hydrocarbon-containing fluid sample and the flow rate of the liquid phase reagent solution for producing the desired slug flow.

In some embodiments, the optical analysis can employ a light source that is part of the downhole tool. The light source may be configured to direct light from the light source to the flow-thru optical cell. In some embodiments, the light source is a visible light source. The visible light source may be configured to emit light in the visible range of the electromagnetic spectrum. In other embodiments, the light source may be configured to emit light in the ultraviolet (UV) range, or the infrared range of the spectrum. In embodiments of the light source configured to emit light on the visible range of the spectrum, the light source may include, but is not limited to, a lamp (e.g., a halogen lamp), a laser, and the like.

In some embodiments, the optical analysis can employ a detector that is part of the downhole tool. In some instances, the detector is a light detector. The light detector may be configured to detect light passing through the flow-thru optical cell for optical analysis of the slug flow passing through the optical cell. In some cases, the detector can be configured to detect light in the visible range of the electromagnetic spectrum. In other cases, the detector can be configured to detect light in the infrared range of the electromagnetic spectrum. In yet other cases, the detector can be configured to detect light in the ultraviolet range of the electromagnetic spectrum. In still other cases, the detector can be configured to detect light in more than one range of the electromagnetic spectrum, such as in the ultraviolet and visible, or the visible and infrared, or the ultraviolet, visible and infrared ranges of the spectrum. In certain embodiments, the detector can be a spectrometer, a bolometer for infrared detection, mercury cadmium telluride and other cooled semiconductor detectors for infrared detection, photodiodes and photomultiplier tubes for visible and ultraviolet detection, and the like.

In some embodiments, the optical analysis can employ a light source and detector that are configured to perform absorption spectroscopy. In this configuration, the light source generates light. The detector measures an incident light spectrum of the light generated by the light source and then re-measures the sample spectrum after placing the sample of interest between the light source and detector. The two measured spectra can then be combined to determine the transmission spectrum of the sample of interest. In certain embodiments, the detector can be configured to measure the transmission spectrum of light for slug flow passing through the optical cell. The transmission spectrum can be processed to determine a shift in SPR peak wavelength. The adsorption of mercury onto nanoparticles can form amalgam nanoparticles that are suspended as a colloid in the liquid phase of the slug flow. The formation of such amalgam nanoparticles may cause the SPR peak wavelength to shift from its original wavelength (e.g., the SPR peak wavelength in the absence of mercury). As such, the shift in the SPR peak wavelength may indicate the presence of mercury in the slug flow. For instance, the shift in the SPR peak wavelength may be proportional to the mass fraction of mercury adsorbed by nanoparticles to form the amalgam nanoparticles, and thus can be used as the basis of quantification of mercury concentration in the slug flow and thus the mercury concentration in the hydrocarbon-containing fluid sample that forms the slug flow.

In some embodiments, the methods can be configured to determine the concentration of mercury in a hydrocarbon-containing fluid sample at concentrations of 1 µg/m$^3$ to 1 g/m$^3$.

Potential Uses

The systems and methods as disclosed herein find use in the detection of mercury in a hydrocarbon-containing fluid sample. As described above, the sample may be a hydrocarbon-containing fluid sample to be tested for the presence of mercury, such as a sample of hydrocarbon gas suspected of containing mercury. For example, the systems and methods as disclosed herein find use in oil field and gas field applications, such as in downhole fluid analysis of formation fluids for the presence of mercury or surface-located facilities that analyze produced fluids for the presence of mercury. It also has other applications in the distribution and storage of hydrocarbon fluids (such as natural gas) for testing the hydrocarbon fluid for the presence of mercury.

EXAMPLES

FIG. 1A depicts a rig 10 suitable for employing certain downhole tool embodiments disclosed herein. In the depiction, rig 10 is positioned over (or in the vicinity of) a subterranean oil or gas formation (not shown). The rig may include, for example, a derrick and a hoisting apparatus for lowering and raising various components into and out of the wellbore 40. A downhole tool 100 is deployed in the wellbore 40. The downhole tool 100 may be connected to the surface, for example, via coiled tubing 50 which is in turn coupled to a coiled tubing truck 55.

During operation, the downhole tool 100 may be lowered into the wellbore 40. In a highly deviated borehole, the downhole tool 100 may alternatively or additionally be driven or drawn into the borehole, for example, using a downhole tractor or other conveyance means. The disclosed embodiments are not limited in this regard. For example, the downhole tool 100 may also be conveyed into the borehole 40 using drill pipe, a wireline cable or other conveyance methodologies.

The example downhole tool 100 described herein may be used to obtain and analyze samples of formation fluids in situ. For example, the formation fluid samples can include natural gas, various gas mixtures, oil or various oil mixtures. The downhole tool 100 can include a probe assembly 102 for establishing fluid communication between the downhole tool 100 and the subsurface formation. During operation, the probe assembly 102 may be extended into contact with the borehole wall 42 (e.g., through a mud cake layer). Formation fluid samples may enter the downhole tool 100 through the probe assembly 102 (e.g., via a pumping or via formation pressure). The downhole tool 100 also includes a mercury detection system 140 (FIG. 1B) for detecting the concentration of mercury in a formation fluid sample that enters the downhole tool 100 through the probe assembly 102.

The probe assembly 102 may include a probe mounted in a frame (the individual probe assembly components are not shown). The frame may be configured to extend and retract radially outward and inward with respect to the sampling tool body. Moreover, the probe may be configured to extend and retract radially outward and inward with respect to the frame. Such extension and retraction may be initiated via an uphole or downhole controller. Extension of the frame into contact with the borehole wall 42 may further support the sampling tool in the borehole as well as position the probe adjacent the borehole wall 42.

In some embodiments, such as those used in low permeability formations, the probe assembly 102 may be replaced by packer assembly (not shown). The disclosed embodiments are not limited in this regard. As is known to those of ordinary skill in the art, a packer assembly, when inflated, is intended to seal and/or isolate a section of the borehole wall to provide a flow area with which to induce fluid flow from the surrounding formation.

The downhole tool 100 can also include a downhole telemetry subsystem (not shown) that communicates data signals and control signals between the downhole tool 100 and a surface-located data acquisition and control system, which can be part of the truck 55 or other surface-located system. The downhole telemetry subsystem can employ a variety of telemetry methods, such as wired telemetry methods that employ telemetry cables, drill pipe that incorporate telemetry cables, or fiber optic cables, and wireless telemetry methods, such as mud-pulse telemetry methods, electromagnetic telemetry methods, and acoustic telemetry methods. The downhole telemetry subsystem can also supply electrical power supply signals generated by a surface-located power source for supply to the downhole tool 100. The surface-located power source can be part of the truck 55 or other surface-located system. The downhole tool 100 can also include a power supply transformer/regulator for transforming the electric power supply signals supplied by the surface-located power source to appropriate levels suitable for use by the electrical components of the downhole tool 100. In alternate embodiments, the downhole tool 100 can include a downhole power source supply (such as a battery or turbine generator and/or energy harvester for logging while drilling tools) that supplies electrical power supply signals to the downhole tool 100.

While FIG. 1A depicts a particular downhole tool 100, it will be understood that the disclosed embodiments are not so limited. For example, downhole tool 100 may include a drilling tool such as a measurement while drilling or logging while drilling tool configured for deployment on a drill string. The disclosed embodiments are not limited in these regards.

Figure 1B:
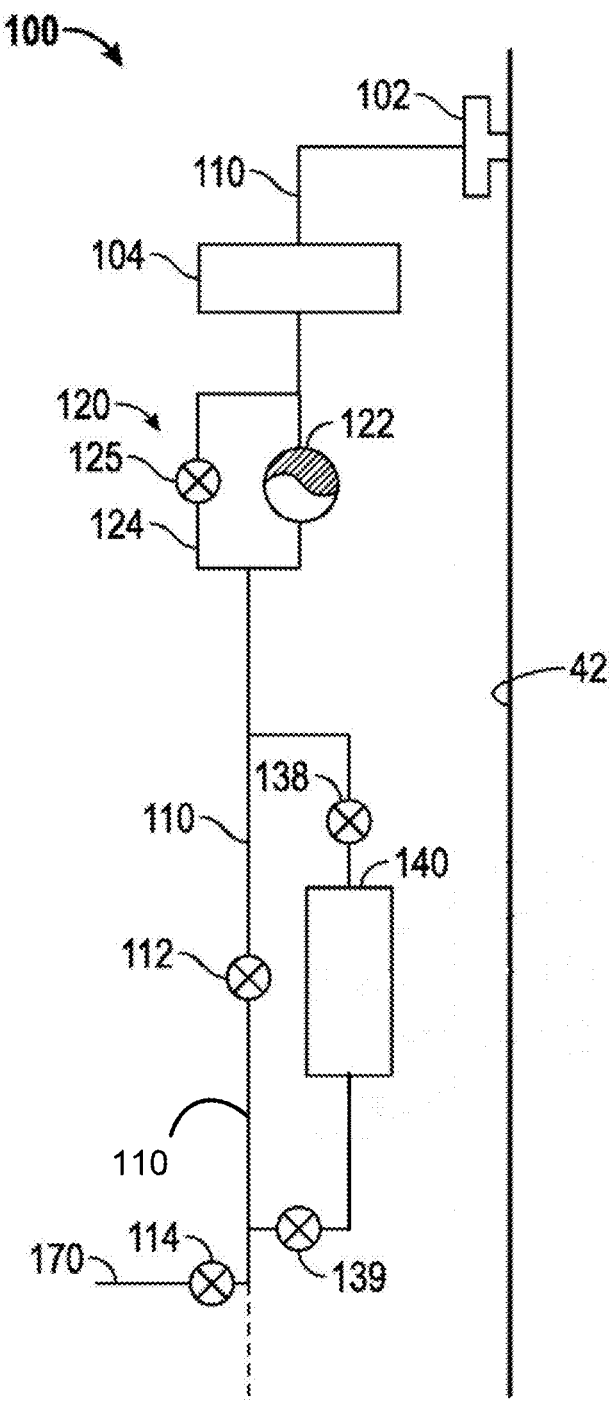
FIG. 1B is a schematic fluid flow circuit diagram of the downhole tool of FIG. 1A.

FIG. 1B shows the fluid flow circuit of the downhole tool 100 of FIG. 1A. The probe assembly 102 is depicted as being in contact with borehole wall 42 for obtaining a formation fluid sample. In the depicted embodiment, probe 102 is in fluid communication with a primary flow line 110 including a fluid analysis module 104 and a fluid pumping module 120. The fluid pumping module 120 is in fluid communication with the probe 102 and includes a pump 122 and a bypass flow line 124 with bypass valve 125 that are coupled in parallel with one another as depicted. A mercury detector 140 is in fluid communication with primary flow line 110 and may be configured to receive a formation fluid sample. The downhole tool 100 can further include an isolation valve 112 that is part of the primary flow line 110 as well as a discharge valve 114 and a fluid outlet line 170 that are fluidly coupled to the primary flow line 110 as shown. The discharge valve 114 and a fluid outlet line 170 can be configured for discharging unwanted formation fluid into the annulus or into the subterranean formation. The downhole tool 100 may further include one or more sample bottles (not shown on FIG. 1B) that are fluidly coupled to the primary flow line 110 by associated valves and have various functionality, such as, for example, zero dead volume (flashing line), self-sealing functionality, and/or being nitrogen-charged as is well known.

The probe assembly 102 may be engaged with the borehole wall 42 as depicted so as to establish fluid communication between the subterranean formation and the primary flow line 110 (those of ordinary skill will readily appreciate that the probe assembly may penetrate a mud cake layer on the borehole wall so as to obtain fluid directly from the formation). Examples of probes suitable for use in the in the disclosed embodiments include the Single-Probe Module or Dual-Probe Module included in the Schlumberger MDT® or described in U.S. Pat. Nos. 4,860,581 and 6,058,773, which are fully incorporated by reference herein. While not depicted it will be understood that the probe assembly may include or more probes coupled to a frame that may be extended and retracted relative to a tool body. In the depicted embodiment, probe assembly 102 is an inlet probe that provides a flow channel from the subterranean formation to the primary flow line 110. The downhole tool 100 may further include one or more outlet probes (e.g., at the downstream end of the fluid outlet line 170) so as to provide a channel through which fluid may flow from the primary flow line 110 out of the tool 100 and back into the formation. In such embodiments, fluid may be circulated from the formation into the primary flow line 110 and back into the formation.

Fluid analysis module 104 may include substantially any suitable fluid analysis sensors and/or instrumentation, for example, including chemical sensors, optical fluid analyzers, optical spectrometers, nuclear magnetic resonance devices, a conductivity sensor, a temperature sensor, a pressure sensor. More generally, fluid analysis module 104 may include substantially any suitable device that yields information relating to the composition of the formation fluid such as the thermodynamic properties of the fluid, conductivity, density, viscosity, surface tension, pressure, temperature, and phase composition (e.g., liquid versus gas composition or the gas content) of the fluid. While not depicted, it will be understood that fluid analysis sensors may alternatively and/or additionally be deployed on the downstream side of the fluid pumping module, for example, to sense fluid property changes that may be induced via pumping.

Fluid pumping module 120 may include substantially any suitable pump 122. For example, the pump 122 may include a reciprocating piston pump, a retractable piston pump, or a hydraulic powered pump.

The mercury detector 140 is fluidly coupled to the primary flow line 110 by an intake valve 138 and an exhaust valve 139. The mercury detector 140 may include a fluidic device that is supplied with a liquid phase reagent solution and a hydrocarbon-containing fluid sample obtained via the probe 102 and the primary flow line 110. The fluidic device is configured to form a gas-liquid slug flow (i.e., a slug flow of a gas-phase and a liquid phase) or liquid-liquid slug flow (i.e., slug flow of two immiscible liquids) from the supplied liquid phase reagent solution and hydrocarbon-containing fluid sample. The fluidic device can include macroscopic or millimeter-sized fluidic channels and conventional flow handling components (capillary tubes, y-junctions, t-junctions, custom manifolds, etc.) that are used to generate the slug flow. The liquid phase reagent solution can include nanoparticles suspended in the liquid phase reagent solution. The nanoparticles of the liquid phase reagent solution of the slug flow can adsorb the mercury of the hydrocarbon-containing fluid sample that is contained in the slug flow. The mercury detector 140 can also include an optical analyzer that performs optical analysis of the slug flow produced by the fluidic device to determine concentration of mercury in the hydrocarbon-containing fluid sample.

Figure 1C:
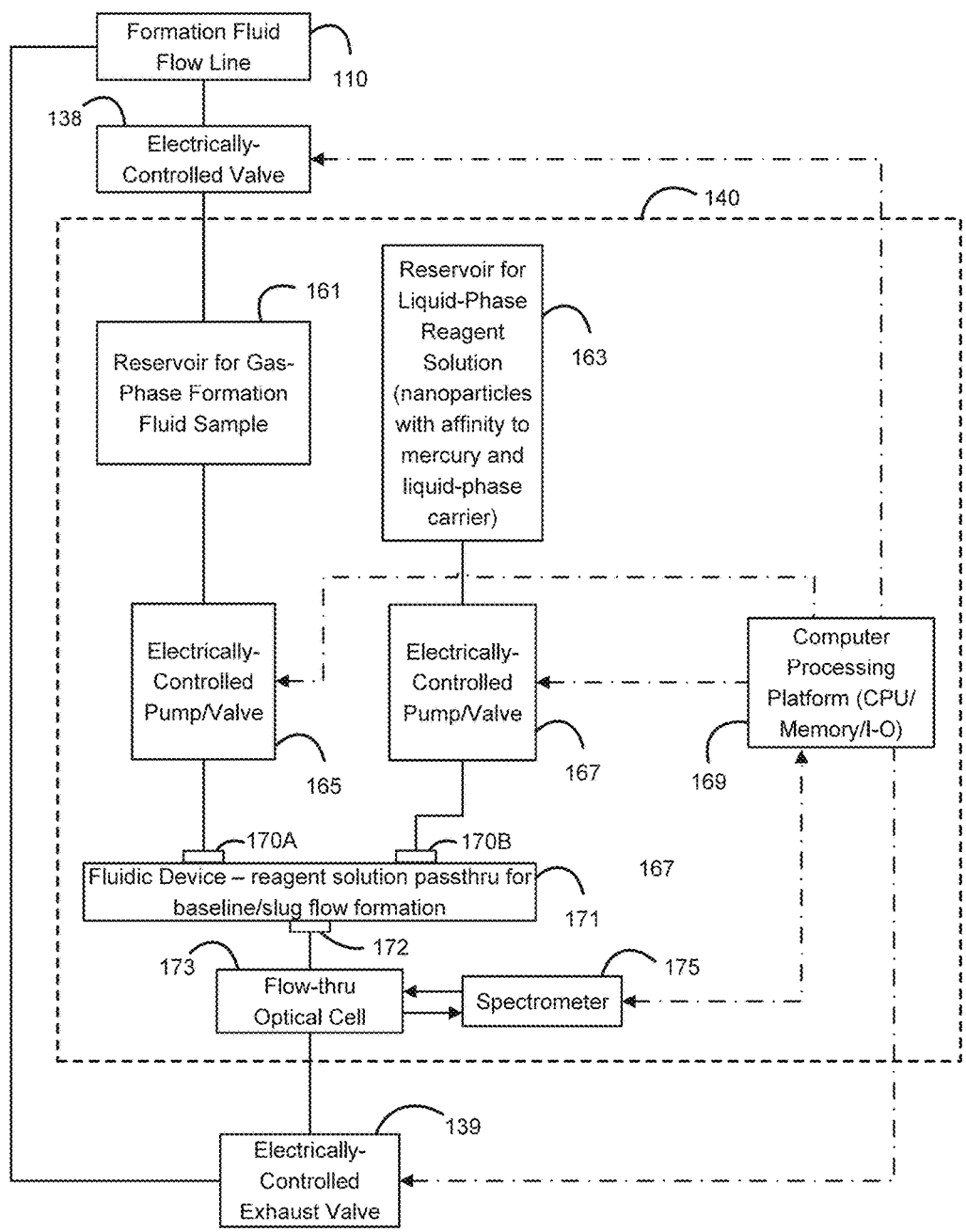
FIG. 1C is a schematic diagram showing one example of a mercury detection system that can be part of the downhole tool of FIG. 1B.

FIG. 1C depicts an illustrative embodiment of the mercury detector 140 of FIG. 1B, which performs automated fluid analysis of a gas phase formation fluid sample to determine the concentration of mercury in the gas phase formation fluid sample. The mercury detector 140 includes a reservoir 161 that is fluidly coupled to the primary flow line 110 via an electrically-controlled intake valve 138. The reservoir 161 can be configured to hold a gas phase formation fluid sample obtained via the probe 102 and the primary flow line 110 of the tool 100. The gas phase formation fluid sample includes gas phase hydrocarbons and possibly other gas phase components (such as mercury vapor). The mercury detector 140 also includes a reservoir 163 that is pre-loaded with a liquid phase reagent solution. The liquid phase reagent solution can include a liquid phase carrier with suspended nanoparticles that have an affinity to mercury. In some embodiments, the liquid phase reagent solution includes water as the liquid phase carrier with suspended nanoparticles of noble metal such as gold, silver, copper or be an oxide, such as zinc oxide and indium tin oxide or combinations thereof. In some embodiments, the nanoparticles can have a concentration of up to $1\times10^{15}$ nanoparticles/cm$^3$ in the liquid phase reagent solution. In some embodiments, the nanoparticles can be formed from a silica core coated with a noble metal (e.g., gold) shell, a noble metal (e.g., gold) core coated with a silica shell, or recursive layers of silica and a noble metal (e.g., gold) possibly with varying thickness. Such nanoparticles can be designed and/or selected to have a particular SPR wavelength, which shifts due to accumulation of mercury thereon as described herein. The liquid phase reagent solution can also include a stabilizer that aids in maintaining the suspension of the nanoparticles at the high temperature conditions commonly found downhole. Note that without such a stabilizer, the high temperature downhole conditions can destabilize the nanoparticles suspended in liquid phase reagent solution and cause precipitation. In some embodiments, the stabilizer can be a polymer soluble in the liquid phase carrier, such as poly(acrylic acid) that is water soluble for the case where water is used the liquid phase carrier.

The reservoir 161 is fluidly coupled to an electrically-controlled pump and valve 165, which are operated to pump a flow of the gas phase formation fluid sample as contained in the reservoir 161 to an input port 170A of the fluidic device 171. A pressure sensor (not shown) can be disposed within flow line output of the pump 165 in order to monitor the pump pressure. Such pump pressure can be can be used as a form of feedback to adjust the operation of the pump 165 in order to maintain pressure levels within the pressure rating of the apparatus 140 and to ensure that the flow of the gas phase formation fluid sample into the input port 170A occurs as desired. In some embodiments, the pump and valve 165 can include an electrically-controlled syringe pump, where the syringe of the pump acts as the reservoir 161 that stores the gas phase formation fluid sample.

The reservoir 163 is fluidly coupled to an electrically-controlled pump and valve 167, which are operated to pump a flow of the liquid phase reagent solution as contained in the reservoir 163 to an input port 170B of the fluidic device 171. A pressure sensor (not shown) can be disposed within flow line output of the pump 167 in order to monitor the pump pressure. Such pump pressure can be can be used as a form of feedback to adjust the operation of the pump 167 in order to maintain pressure levels within the pressure rating of the apparatus 140 and to ensure that the flow of the liquid phase reagent solution into the input port 170B occurs as desired. In some embodiments, the pump and valve 167 can include an electrically-controlled syringe pump, where the syringe of the pump acts as the reservoir 163 that stores the liquid phase reagent solution.

The fluidic device 171 produces a gas-liquid slug flow from the gas phase formation fluid sample introduced into the inlet port 170A and the liquid phase reagent solution introduced into the inlet port 170B. The gas phase of the slug flow is formed from the gas phase formation fluid sample introduced into the inlet port 170A, and the liquid phase of the slug flow is formed from the liquid phase reagent solution introduced into the inlet port 170B. The fluidic device 171 also provides for enhanced mass transfer of any mercury vapor of the gas phase of the slug flow to the nanoparticles of the liquid phase of the slug flow to allow the mercury to absorb on the nanoparticles to form amalgam nanoparticles, which are suspended as a colloid in the liquid phase of the slug flow. The fluidic device 171 also includes an outlet port 172 that provides an outlet for the slug flow produced by the fluidic device 171. Such slug flow carries the amalgam nanoparticles as a colloid in the liquid phase of the slug flow where the degree of accumulation of mercury into the nanoparticles in the liquid phase of the slug flow is proportional to the concentration of the mercury vapor in the gas phase formation fluid sample.

In some embodiments, the slug flow produced by the fluidic device 171 can be controlled by the flow rate of the gas phase formation fluid sample pumped into the inlet port 170A by operation of the pump 165 and/or the flow rate of the liquid phase reagent solution pumped into the inlet port 170B by operation of the pump 167. The slug flow can be influenced by certain properties (such as viscosity or surface tension) of formation fluid sample that can vary across samples. One or more of such properties can be measured by the fluid analysis module 104 of the downhole tool and such property measurements can be used as inputs to determine the appropriate class of formation fluid sample type and the pump control settings for the pump 165 and/or pump 167 that dictate the flow rate of the gas phase formation fluid sample pumped into the inlet port 170A by operation of the pump 165 and/or the flow rate of the liquid phase reagent solution pumped into the inlet port 170B by operation of the pump 167 in order to produce the desired slug flow.

The outlet port 172 of the fluidic device 171 is fluidly coupled to the inlet of a flow-thru optical cell 173. A spectrometer 175 is optically coupled to the flow-thru optical cell 173 and can be configured to determine an optical spectrum of the slug flow that flows from the outlet port 172 of the fluidic device 171 and through the flow-thru optical cell 173. The slug flow that passed through the flow-thru optical cell 173 carries the amalgam nanoparticles as a colloid in the liquid phase of the slug flow where the degree of accumulation of mercury into the nanoparticles in the liquid phase of the slug flow is proportional to the concentration of the mercury vapor in the gas phase formation fluid sample.

An electrically-controlled exhaust valve 139 can be fluidly coupled to the outlet of the flow-thru optical cell 173 to direct the slug flow to the flow line 110 for discharge as waste via the discharge valve 114 and a fluid outlet line 170.

The mercury detector 140 can also include a computer processing platform 169 that interfaces to the electrically-controlled intake valve 138, the electrically-controlled pump and valve 165, the electrically-controlled pump and valve 167, the spectrometer 175, the electrically controlled exhaust valve 139 and to other parts of the downhole tool 100 (such as the telemetry subsystem of the tool) via suitable signal paths, such as wired or wireless data connections. The computer processing platform 169 can also interface to other components (such as the fluid analysis module 104) of the downhole tool, if desired. The computer processing platform 169 can include a CPU, computer memory (including persistent and possibly non-persistent memory) and Input-Output (or I-O) functionality that is programmed with suitable control logic to carry out a variety of functions. The control logic of the computer processing platform 169 (which can be embodied in software that is loaded from persistent memory and executed by the CPU of the computer processing platform 169) can be configured to control the different parts of the mercury detector 140 to carry out an automated sequence of operations that obtains a gas phase formation sample and determines the concentration of the mercury vapor in the gas phase formation fluid sample. In some embodiments, the automated sequence of operations includes i) loading a gas phase formation fluid sample into the reservoir 161, ii) pumping the gas phase formation fluid sample as well as the liquid phase reagent solution held in the reservoir 163 to the fluidic device 171 to produce the slug flow, which carries the amalgam nanoparticles as a colloid in the liquid phase of the slug flow where the degree of accumulation of mercury into the nanoparticles in the liquid phase of the slug flow is proportional to the concentration of the mercury vapor in the gas phase formation fluid sample, iii) operating the spectrometer 175 to obtain an optical spectrum of the slug flow as it flows through an optical flow-thru cell, and iv) operating the computer processing platform 169 to process the optical spectrum obtained by the spectrometer 175 to determine the concentration of the mercury vapor in the gas phase formation fluid sample. The computer processing platform 169 can also store in computer memory data representing the concentration of the mercury vapor in the gas phase formation fluid sample for output to the surface-located data acquisition and control system for reservoir analysis.

Figure 2A:
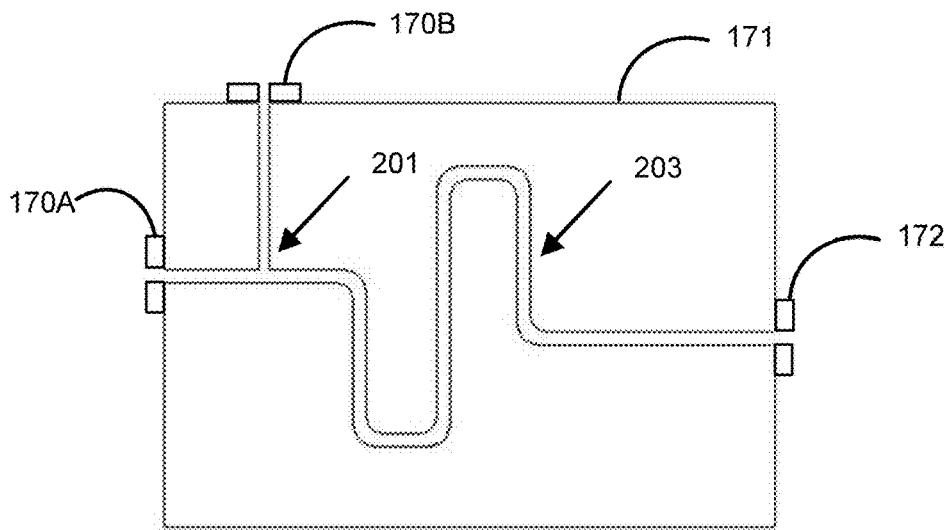
FIG. 2A is a schematic diagram showing one example of a fluidic device that can be part of the mercury detection system of FIG. 1C.
Figure 2B:
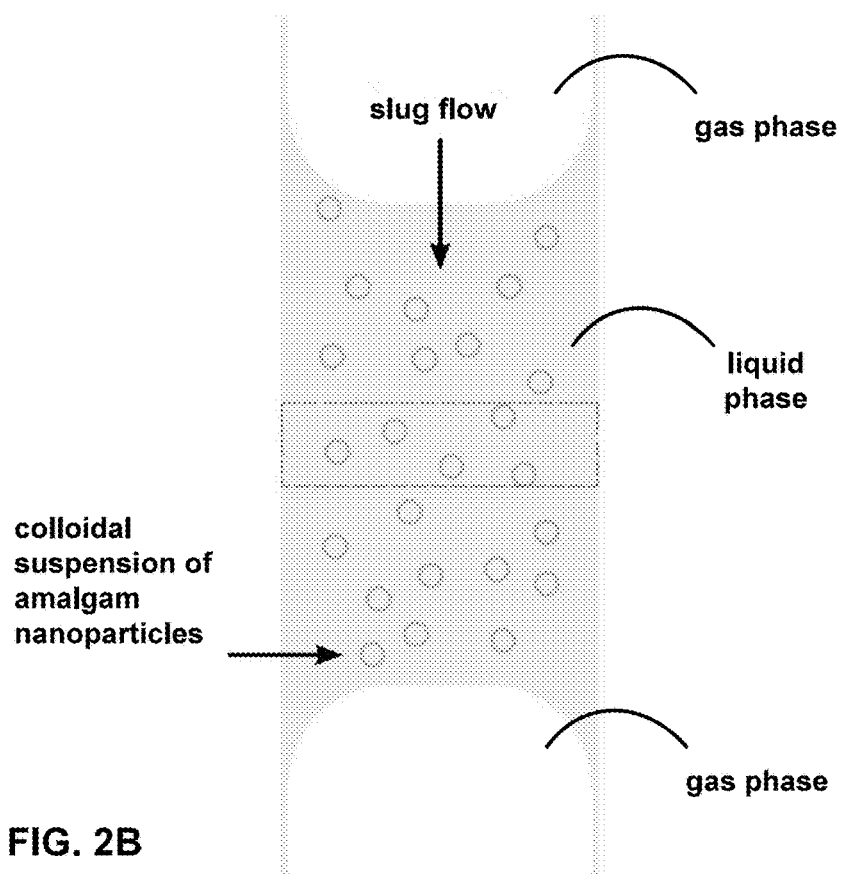
FIG. 2B is a schematic diagram of slug flow produced by the fluidic device of the mercury detection system of FIG. 1C.

FIG. 2A is a schematic diagram showing one example of the fluidic device 171 of FIG. 1C, which includes an internal mixer section 201 and an internal reactor section 203. The mixer section 201 is a T-type channel junction that produces a gas-liquid slug flow from the gas phase formation fluid sample introduced into the inlet port 170A and the liquid phase reagent solution introduced into the inlet port 170B. The gas phase of the slug flow is formed from the gas phase formation fluid sample introduced into the inlet port 170A, and the liquid phase of the slug flow is formed from the liquid phase reagent solution introduced into the inlet port 170B. The reactor section 203 is a channel that provides a flow path that allows for mass transfer of the mercury vapor of the gas phase of the slug flow to the nanoparticles of the liquid phase of the slug flow to allow the mercury to absorb on the nanoparticles to form amalgam nanoparticles. Such amalgam nanoparticles are suspended as a colloid in the liquid phase of the slug flow as shown in FIG. 2B. Note that the amalgam nanoparticles and flow channel of FIG. 2B are not shown to scale. The liquid phase of the slug flow can be a continuous phase that wets the wall(s) of the channel of the reactor section 203, while the gas phase of the slug flow forms slugs or bubbles that are separated from the wall(s) of the channel of the reactor section 203 by a thin layer of the continuous liquid phase. In some embodiments, the length of the gas phase slugs or bubbles in the slug flow is several times longer than the channel diameter of the reactor section 203, and the diameter of the gas phase slugs or bubbles in the slug flow is almost equal to the channel diameter of the reactor section 203 such that a thin liquid film separates the gas from the wall(s) of the channel of the reactor section 203. The outlet port 172 at the downstream end of the flow path of the reactor section 203 provides an outlet for the slug flow produced by the fluidic device 171. In some embodiments, the fluidic device 171 of FIG. 2C can be realized by a microfluidic device as described above.

Figure 2C:
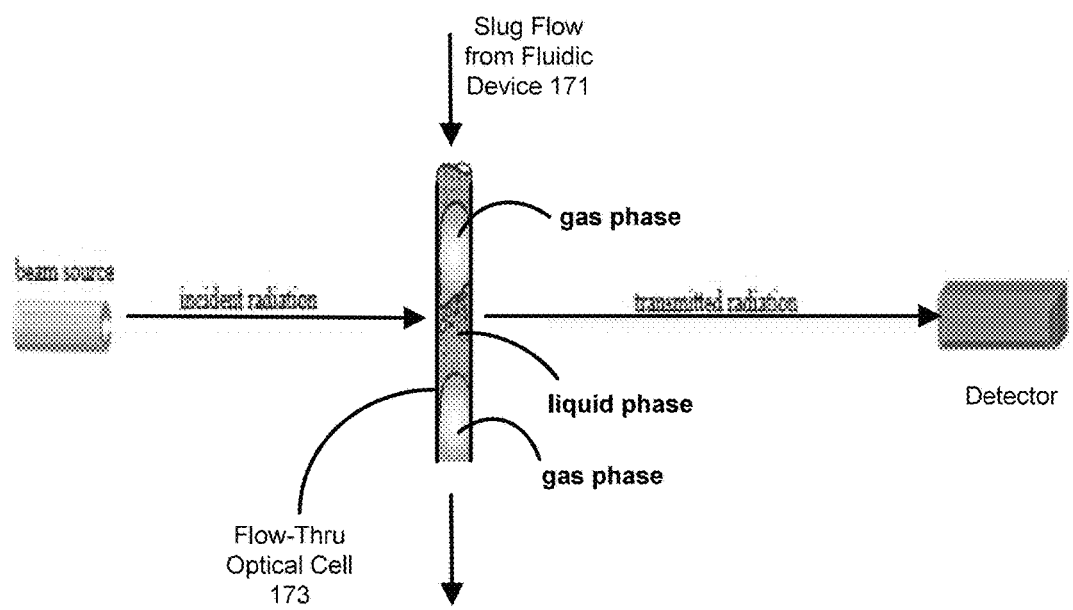
FIG. 2C is a schematic diagram showing one example of an optical analyzer that can be part of the mercury detection system of FIG. 1C. Note that the amalgam nanoparticles and the flow channel of FIG. 2C are not drawn to scale. Furthermore, the gas slugs can be well formed (i.e., round on both sides) with no small bubbles of gas as shown in the figure.

FIG. 2C is a schematic diagram showing one example of the flow-thru optical cell 173 and spectrometer 175 of FIG. 1C. The spectrometer 175 includes a light source (or beam source) that directs a beam of incident radiation toward the flow-thru optical cell 173. The slug flow supplied from the outlet port 172 of the fluidic device 171 flows through the flow-thru optical cell 173 and interacts with the incident radiation. The incident radiation is absorbed as a function of frequency or wavelength due to its interaction with the slug flow. Such absorption effects the transmitted radiation (i.e., the incident radiation transmitted thru the flow-thru optical cell 173) that is received by a detector for processing that derives an optical spectrum of the slug flow. The computer processing platform 169 can also be configured to process the optical spectrum obtained by the spectrometer 175 to determine the concentration of the mercury vapor in the gas phase formation fluid sample.

In some embodiments, the computer processing platform 169 can process the optical spectrum obtained by the spectrometer 175 to determine a shift in the SPR peak wavelength that occurs due to a change in the permittivity of the suspended nanoparticles of the liquid phase of the slug flow as the mercury is adsorbed resulting in amalgam nanoparticles. More specifically, as the amalgam nanoparticles form, the complex permittivity of the nanoparticles changes from that of the native material (e.g., gold) to that of the amalgam (e.g., gold/mercury nanoparticle, limited in part by the concentration of mercury in solution). This change in permittivity will change the condition for SPR coupling, which causes a spectral shift in the SPR wavelength. And the spectral shift in the SPR wavelength can be correlated to original mercury concentration in the hydrocarbon fluid.

In some embodiments, the spectral shift in the SPR wavelength can be determined by measuring the light loss at each wavelength, with the maximum loss occurring due to SPR coupling. For example, the spectral shift in the SPR wavelength can be determined by measuring a change in spectral absorbance. For very small nanoparticles (R<12 nm for gold nanoparticles), a wavelength dependent attenuation of light intensity $A(\lambda)$ can be described as:

$$A(\lambda) = \log_{10} \frac{I_o(\lambda)}{I_d(\lambda)} = \frac{\sigma_{ext}(\lambda) N d}{2.303}, \quad (1a)$$

$$\sigma_{ext}(\lambda) = \frac{24\pi^2 R^3 \varepsilon_s(\lambda)^{3/2}}{\lambda} \frac{\varepsilon''_m(\lambda)}{[\varepsilon'_m(\lambda) + 2\varepsilon_s(\lambda)]^2 + \varepsilon''_m(\lambda)^2} \quad (1b)$$

where $I_o(\lambda)$ is the incident light intensity at wavelength $\lambda$,
$I_d(\lambda)$ is the transmitted light intensity at wavelength $\lambda$ across an optical path length of d,
N is the number of particles per unit volume,
$\sigma_{ext}(\lambda)$ is the extinction cross section of a single particle at wavelength $\lambda$ and a radius R,
$\varepsilon_s(\lambda)$ is the real component of permittivity of the surrounding media at wavelength $\lambda$, and
$\varepsilon_m(\lambda)$ is the effective permittivity of the nanoparticle at wavelength $\lambda$, which can be represented by the complex dielectric function of the form $\varepsilon_m(\lambda)=\varepsilon'_m(\lambda)+i\varepsilon''_m(\lambda)$, where $\varepsilon'_m(\lambda)$ is the real component of the permittivity of the nanoparticle at wavelength $\lambda$ and $\varepsilon''_m(\lambda)$ is the imaginary component of the permittivity of the nanoparticle at wavelength $\lambda$.

It should be noted that the permittivity of the nanoparticles is size dependent and at the nanoscale it is different from macroscopic bulk properties. For particle diameters less than electronic mean free path, ~20 nm for gold, this is otherwise known as the intrinsic size-effect.

Note that $\varepsilon_m(\lambda)$ changes as the mercury is accumulated by the nanoparticle and the amalgam forms (from the initial state where the nanoparticle is pure metal to an equilibrium amalgam nanoparticle), the wavelength dependent attenuation will also shift. The magnitude or degree of the shift in the SPR wavelength will enable direct quantification of elemental mercury concentration in the surrounding slug or bubble (knowing the confined volume of the slugs/channel), which can be used to determine elemental mercury concentration in the gas phase formation sample.

Figures 3A, 3B, 3C:
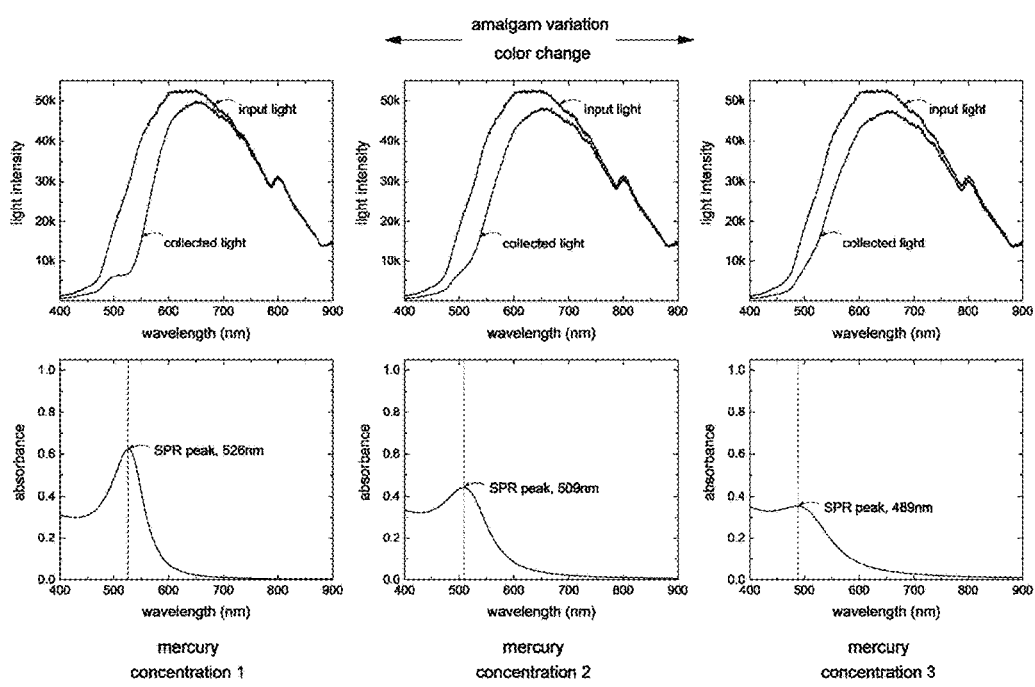
FIGS. 3A, 3B and 3C are example graphs of the incident light intensity spectrums and transmitted light intensity spectrums together with corresponding SPR peak wavelengths for three different mercury concentrations (mg/m$^3$) as determined from optical analysis according to embodiments of the present disclosure.

FIGS. 3A, 3B and 3C depict graphs of incident light intensity spectra (incident light intensity over a range of wavelengths labeled "input light") and the transmitted light intensity spectra (transmitted light intensity over the range of wavelengths labeled "collected light") as measured by the spectrometer 175 for three different mercury concentrations (mg/m³). FIGS. 3A, 3B and 3C also depict graphs that show the SPR peak wavelength determined by processing the corresponding incident light intensity spectrum and transmitted light spectrum for the three different mercury concentrations (mg/m³). Specifically, the bottom graph of FIG. 3A shows the SPR peak wavelength determined by processing the incident light intensity spectrum and the transmitted light spectrum shown in the top graph of FIG. 3A for a particular mercury concentration labeled "concentration 1." The bottom graph of FIG. 3B shows the SPR peak wavelength determined by processing the incident light intensity spectrum and the transmitted light spectrum shown in the top graph of FIG. 3B for another particular mercury concentration labeled "concentration 2". And the bottom graph of FIG. 3C shows the SPR peak wavelength determined by processing the incident light intensity spectrum and the transmitted light spectrum shown in the top graph of FIG. 3C for yet another particular mercury concentration labeled "concentration 3". In each case, the shift of the SPR peak wavelength relative to the SPR peak wavelength of an incident light intensity spectrum and transmitted light spectrum for a baseline experiment that involves only the liquid phase reaction solution can be calculated, and this shift in SPR peak wavelength can be correlated to elemental mercury concentration in the surrounding slug or bubble, which can be used to determine elemental mercury concentration in the gas phase formation sample.

Figure 3D:
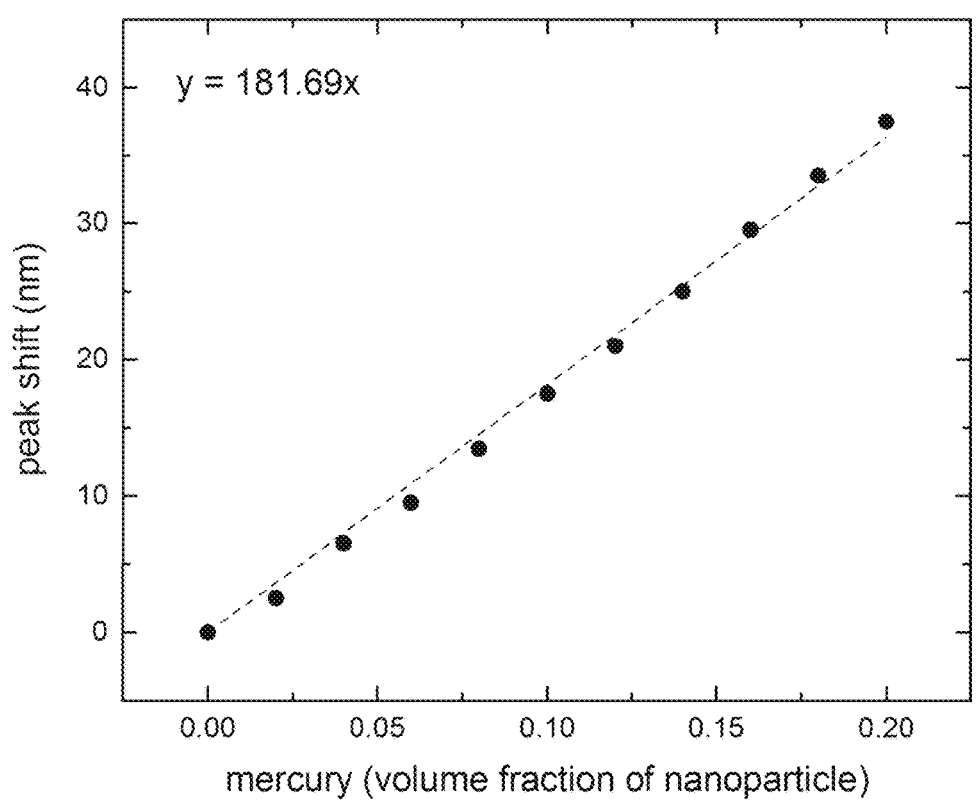
FIG. 3D is a graph showing correlation between shift in SPR peak wavelength and mercury concentration.

FIG. 3D illustrates an example correlation function that can be used to correlate a shift in SPR peak wavelength to elemental mercury concentration in the surrounding slug or bubble. In this example, a linear fit is used between SPR peak wavelength shift and the mercury volume fraction of the nanoparticle—representative of concentration in the original sample for a fixed volume slug. However, other fitting approaches (polynomial, etc.) may be suitable for targeting other concentration ranges and/or experimental details. Those skilled in the art may recognize that other shape metrics can also be used, such as peak width.

Note that control logic of the downhole tool 100 as described above can be implemented as computer program executed by the computer processing platform 169. The computer program may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processing platform. The computer instructions may be distributed in any form as a removable storage medium with accompanying printed or electronic documentation (e.g., shrink wrapped software), preloaded with a computer system (e.g., on system ROM or fixed disk), or distributed from a server over a communication system (e.g., the Internet or World Wide Web).

The computer processing platform 169 may include a CPU, other integrated circuitry (e.g., Application Specific Integrated Circuits (ASIC)), programmable logic devices (e.g., a Field Programmable Gate Arrays (FPGA) and/or discrete electronic components coupled to a printed circuit board. Any of the methods and processes described above can be implemented using such logic devices.

Figure 4:
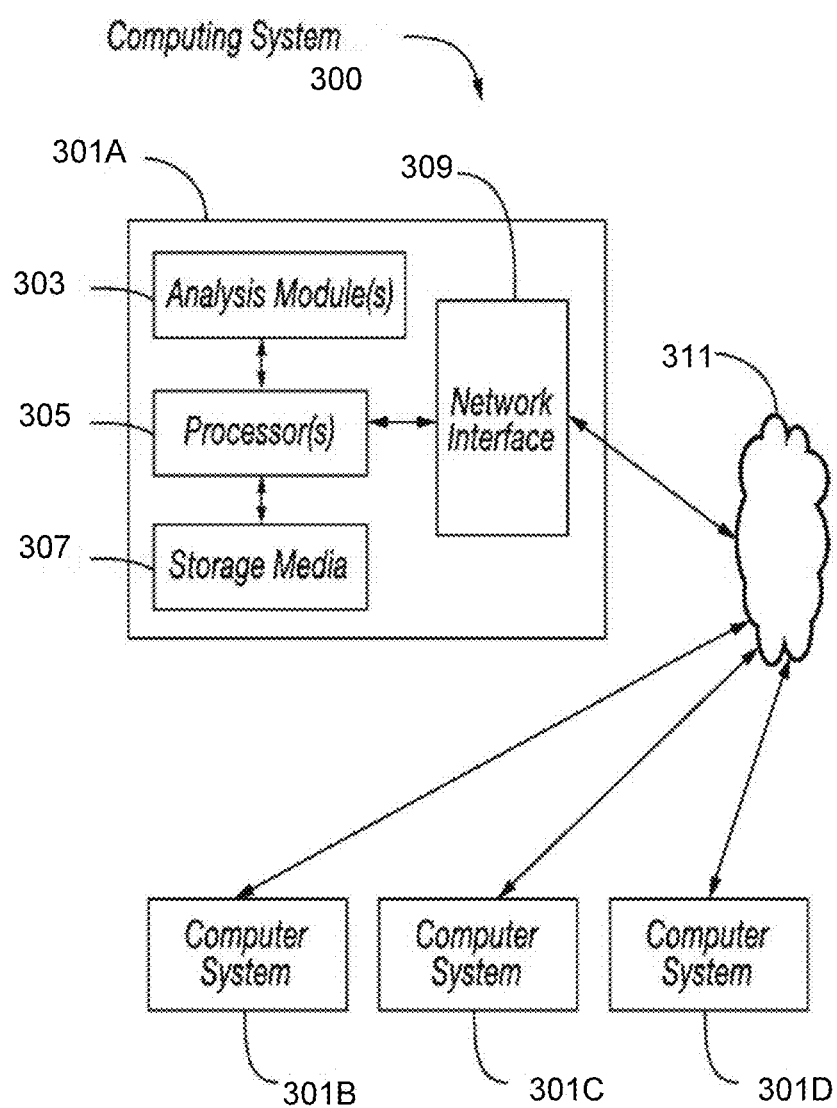
FIG. 4 is a schematic block diagram of an example computer processing system that can be part of the mercury detection system according to embodiments of the present disclosure.

FIG. 4 shows an example computing system 300 that can be used to implement the computer processing platform 169 as described herein. The computing system 300 can be an individual computer system 301A or an arrangement of distributed computer systems. The computer system 301A includes one or more analysis modules 303 (a program of computer-executable instructions and associated data) that can be configured to perform various tasks according to some embodiments, such as the tasks described above. To perform these various tasks, an analysis module 303 executes on one or more processors 305, which is (or are) connected to one or more storage media 307. The processor(s) 305 is (or are) also connected to a network interface 309 to allow the computer system 301A to communicate over a data network 311 with one or more additional computer systems and/or computing systems, such as 301B, 301C, and/or 301D. Note that computer systems 301B, 301C and/or 301D may or may not share the same architecture as computer system 301A, and may be located in different physical locations.

The processor 305 can include at least a microprocessor, microcontroller, processor module or subsystem, programmable integrated circuit, programmable gate array, digital signal processor (DSP), or another control or computing device.

The storage media 307 can be implemented as one or more non-transitory computer-readable or machine-readable storage media. Note that while in the embodiment of FIG. 4, the storage media 307 is depicted as within computer system 301A, in some embodiments, storage media 307 may be distributed within and/or across multiple internal and/or external enclosures of computing system 301A and/or additional computing systems. Storage media 307 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 303 can be provided on one computer-readable or machine-readable storage medium of the storage media 307, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 300 is only one example of a computing system, and that computing system 300 may have more or fewer components than shown, may combine additional components not depicted in the embodiment of FIG. 4, and/or computing system 300 may have a different configuration or arrangement of the components depicted in FIG. 4. The various components shown in FIG. 4 may be implemented in hardware, software, or a combination of both hardware and software, including one or more signal processing and/or application specific integrated circuits.

Figure 5A:
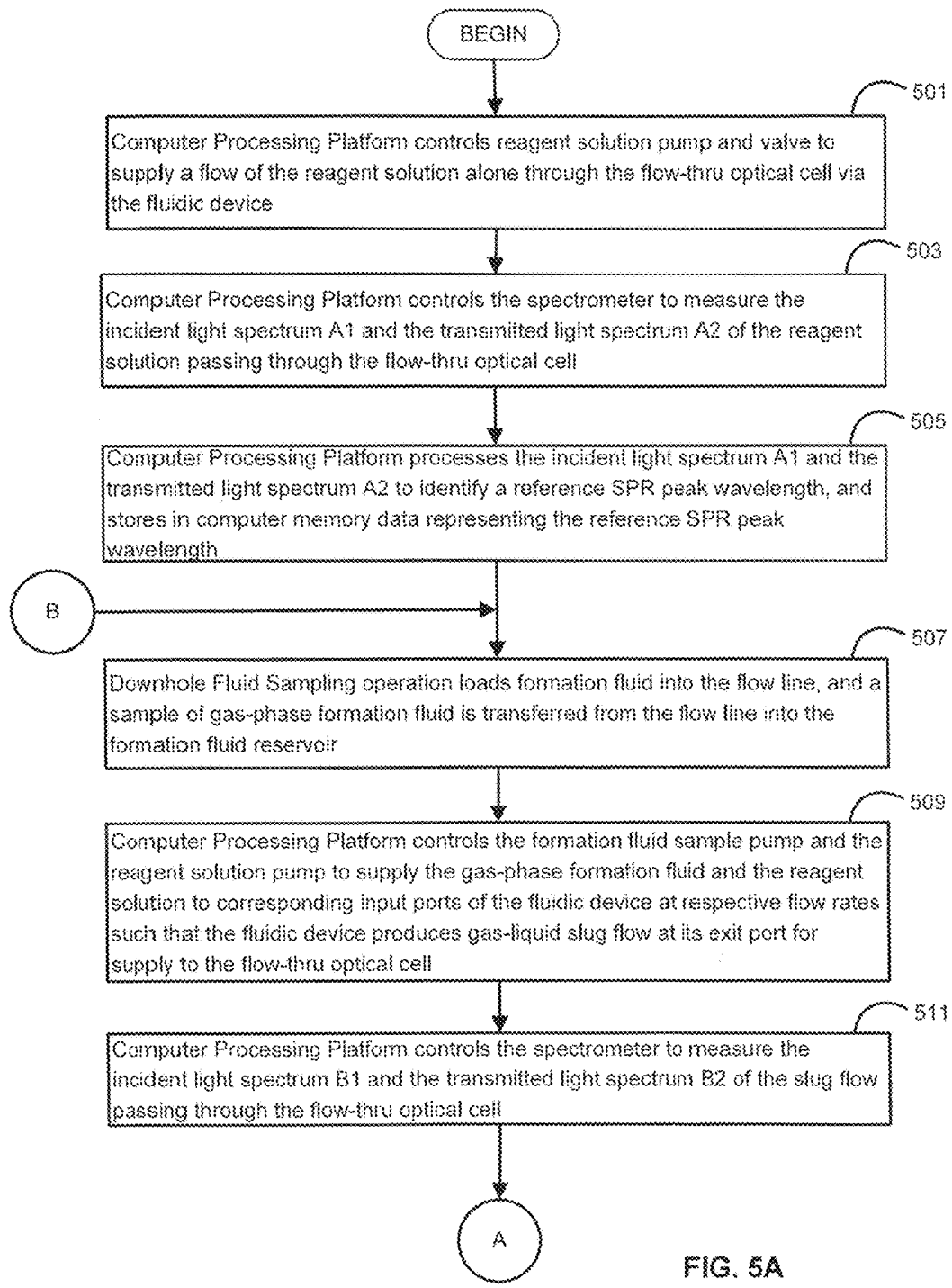
FIGS. 5A and 5B, collectively, is a flow chart illustrating an automated sequence of operations carried out by the downhole tool of FIGS. 1B and 1C according to embodiments of the present disclosure.
Figure 5B:
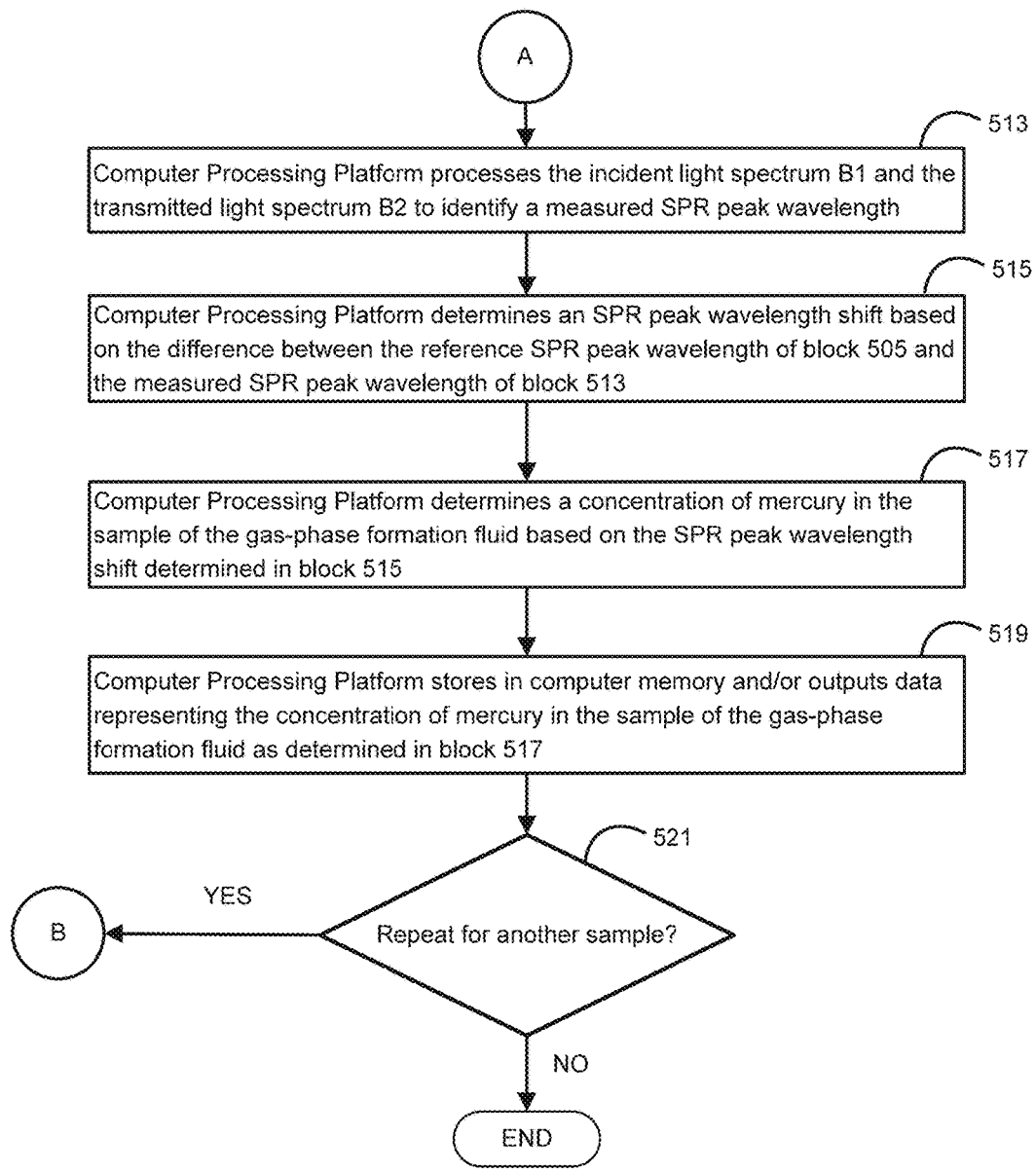

FIGS. 5A and 5B depict an automated sequence of operations carried out by the computer processing platform 169 that controls different parts of the mercury detector 140 to obtain a gas phase formation sample and determine the concentration of the mercury vapor in the gas phase formation fluid sample. The operations begin in block 501 where the computer processing platform 169 controls the reagent solution pump and valve 167 to pump the liquid phase reagent solution held in the reservoir 163 to the input port 170B of the fluidic device 171. The computer processing platform 169 can also control the valve 165 to isolate the reservoir 161 from the input port 170A of the fluidic device 171. Such operations flow the liquid phase reagent solution alone (without any formation fluid) through the fluidic device 171 to the output port 172 for supply to the flow-thru optical cell 173, where the liquid phase reagent solution alone flows through the flow-thru optical cell 173.

In block 503, with the liquid phase reagent solution alone flowing through the flow-thru optical cell 173, the computer processing platform 169 controls the spectrometer 175 to measure the incident light spectrum A1 and the transmitted light spectrum A2 of the reagent solution passing through the flow-thru optical cell 173.

In block 505, the computer processing platform 169 processes the incident light spectrum A1 and the transmitted light spectrum A2 to identify a reference SPR peak wavelength, and stores in computer memory data representing the reference SPR peak wavelength. In some embodiments, the absorbance spectrum can be calculated as per Eqn. 1a above, where the logarithm base 10 is taken of the input intensity spectrum and divided by the transmitted intensity spectrum to yield an absorbance spectrum. The absorbance spectrum can then be analyzed with peak finding algorithms. For example, the derivative of the absorbance spectrum can be calculated. The first derivative could then be smoothed by applying a Savitzky-Golay filter with appropriate parameters. The algorithm would then look for zero-crossings in the first derivative data signifying minima and maxima on the original absorbance spectrum. The algorithm would only select downward zero-crossings (maxima on absorbance spectrum) and only take those zero-crossings where the slope exceeds a predetermined minimum called the slope threshold. At the same zero crossing, an amplitude threshold can be specified on the original absorbance spectrum to make sure the peak is of sufficient amplitude. By specifying the criteria for the smoothing filter, the slope threshold and the amplitude threshold, it is possible to identify the reference SPR peak wavelength. It will be appreciated that such peak finding algorithms are readily available and implemented by those skilled in the art.

In block 507, the downhole tool is configured to perform a downhole fluid sampling operation that loads formation fluid into the primary flow line 110. Furthermore, the computer processing platform 169 opens the valve 138 to transfer a sample of gas-phase formation fluid from the primary flow line 110 into the formation fluid reservoir 161. The loading of the formation fluid into the primary flow line 110 can involve operating the pump 122 to pump formation fluid via the probe 102 through the fluid analysis module 104 until a desired fluid property is obtained. For example, such pumping operation can be intended to obtain virgin gas formation fluid substantially free of drilling fluid contamination. In some embodiments, after obtaining the desired formation fluid, the pump 122 may be shut down. Valves 112 and/or 114 may also be closed as the pump 122 is shut down. The bypass valve 125 may be opened enabling formation fluid to flow from the probe 102 through the bypass flow line 124 to the secondary leg of the primary flow line 110. In another embodiment, after obtaining the desired formation fluid, valves 112 and/or 114 may also be closed but the pump 122 continues operating to enable formation fluid to flow from the probe 102 to the secondary leg of the primary flow line 110.

In block 509, the computer processing platform 169 controls the formation fluid sample pump and valve 165 and the reagent solution pump and valve 167 to supply the gas-phase formation fluid and the reagent solution to corresponding input ports 170A, 170B of the fluidic device 171 at respective flow rates such that the fluidic device 171 produces the gas-liquid slug flow at its output port 172 for supply to the flow-thru optical cell 173. The slug flow passes through the flow-thru optical cell 173 for analysis by the spectrometer 175. The slug flow that is produced by the fluidic device 171 and passes through the flow-thru optical cell 173 carries the amalgam nanoparticles as a colloid in the liquid phase of the slug flow where the degree of accumulation of mercury into the nanoparticles in the liquid phase of the slug flow is proportional to the concentration of the mercury vapor in the gas phase formation fluid sample.

In block 511, the computer processing platform 169 controls the spectrometer to measure the incident light spectrum B1 and the transmitted light spectrum B2 of the slug flow passing through the flow-thru optical cell 173.

In block 513, the computer processing platform 169 processes the incident light spectrum B1 and the transmitted light spectrum B2 to identify a measured SPR peak wavelength. Similar to the embodiment described in block 505, the absorbance spectrum can be calculated as per Eqn. 1a above, where the logarithm base 10 is taken of the input intensity spectrum and divided by the transmitted intensity spectrum to yield an absorbance spectrum. The absorbance spectrum can then be analyzed with peak finding algorithms. For example, the derivative of the absorbance spectrum can be calculated. The first derivative could then be smoothed by applying a Savitzky-Golay filter with appropriate parameters. The algorithm would then look for zero-crossings in the first derivative data signifying minima and maxima on the original absorbance spectrum. The algorithm would only select downward zero-crossings (maxima on absorbance spectrum) and only take those zero-crossings where the slope exceeds a predetermined minimum called the slope threshold. At the same zero crossing, an amplitude threshold can be specified on the original absorbance spectrum to make sure the peak is of sufficient amplitude. By specifying the criteria for the smoothing filter, the slope threshold and the amplitude threshold, it is possible to identify the measured SPR wavelength. It will be appreciated that such peak finding algorithms are readily available and implemented by those skilled in the art.

In block 515, the computer processing platform 169 determines an SPR peak wavelength shift based on the difference between the reference SPR peak wavelength of block 505 and the measured SPR peak wavelength of block 513. Note that blocks 511 to 515 can be repeated for a number of times in order to determine an effective or average SPR peak wavelength shift in block 515.

In block 517, the computer processing platform 169 determines a concentration of mercury in the sample of the gas-phase formation fluid based on the SPR peak wavelength shift determined in block 515. Such determination can be based on a correlation function of SPR peak wavelength shift to mercury concentration, for example, as shown in FIG. 3D.

In block 519, the computer processing platform 169 stores in computer memory and/or outputs data representing the concentration of mercury in the sample of the gas-phase formation fluid as determined in block 517.

In block 521, the computer processing platform 169 can determine whether to repeat the operations of block 507 to 519 for another gas phase formation fluid sample. Such determination can be coordinated by operator input or determined automatically as part of an automatic test sequence. If so, the operations return to block 507 to repeat the operations of block 507 to 519 for another gas phase formation fluid sample. If not, the automated sequence of operations of FIGS. 5A and 5B end.

Figure 6A:
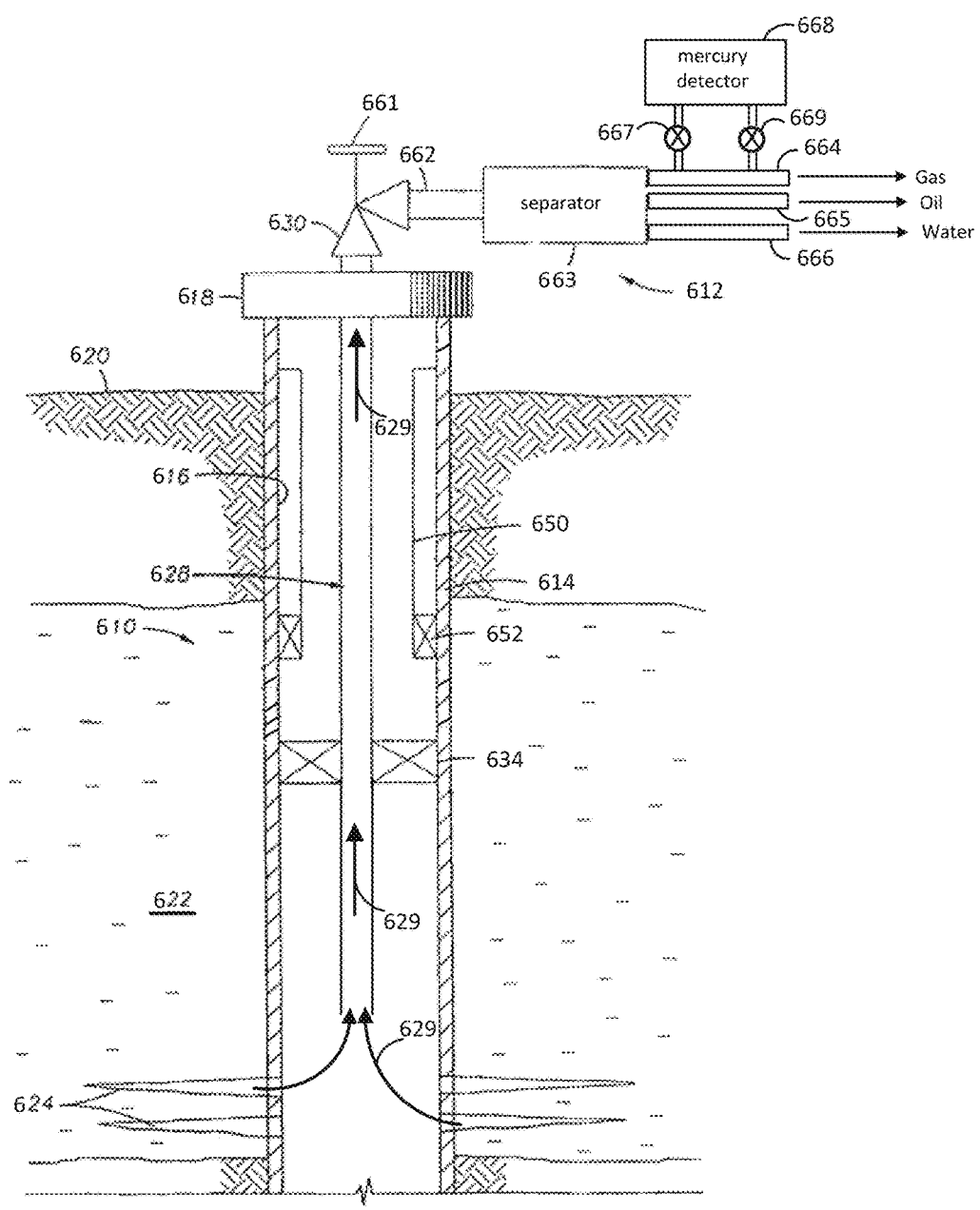
FIG. 6A is a schematic diagram showing one example of a production well in which disclosed surface-located mercury detector embodiments may be utilized.

Referring to FIG. 6A, an exemplary hydrocarbon production well 610 is shown, which includes a wellbore casing 614, which typically includes a number of concentric casing strings (not shown). The casing 614 defines an annulus 616 that extends downward from a wellbore opening or entrance 618 at the surface 620. It is noted that the surface 620 may be either the surface of the earth, or, in the case of a subsea well, the seabed. The casing 614 extends through a hydrocarbon production zone 622 from which it is desired to acquire production fluid. The casing 614 has perforations 624 disposed therethrough so that production fluid may enter the annulus 616 from the production zone 622.

Production tubing 628 is disposed downward within the annulus 616 supported from a wellhead 630 at the surface 620. A production tubing packer 634 is set above the perforations 624 to establish a fluid seal between the production tubing 628 and the casing 614. The production tubing 628 includes at least one fluid inlet below the packer 634 which permits fluid communication from the annulus 616 into the interior of the production tubing 628 to allow production fluid to flow to the wellhead 630 (indicates as arrows 629) due to the formation pressure. In other embodiments, artificial lift (such sucker-rod (beam) pumping, electrical submersible pumping (ESP), gas lift and intermittent gas lift, reciprocating and jet hydraulic pumping systems, plunger lift, and progressive cavity pumps (PCP)), can be used to generate or assist in flowing the production fluid through the interior of the production tubing 628 to the wellhead 630.

The upper portion of the production tubing 628 may optionally be surrounded by liner or sleeve 650 which extends from the well opening 618 downward within the annulus 616. A packer 652 can be set at the lower end of the sleeve 650 to establish a fluid seal between the sleeve 650 and the casing 614. The sleeve 650 can provide additional isolation between the annulus 616 and any fresh water aquifers.

The wellhead 630 can include an adjustable choke 661 of a type known in the art which is used to control the flow of production fluids through the wellhead 630. A lateral fluid flowline 662 extends from the wellhead 630 to the separator assembly 663.

The separator assembly 663 separates the gas, oil and water components of the production fluids supplied thereto, which are output by corresponding flowlines 664, 665 and 666 as shown. The flowlines 664, 665 and 666 carry the respective gas, oil and water components of the production fluids to other surface-located facilities (not shown). Such surface-located facilities can include fluid collection systems (such as tanks), fluid processing devices and/or pipelines.

A mercury detector 668 is fluidly coupled to the flow line 664 by an intake valve 667 and an exhaust valve 669. The mercury detector 668 can be configured to receive a sample of the gas component of the produced fluids (referred to herein as "sample of produced gas" or "produced gas sample") that is output by the separator 663 and carried by the flowline 664. The mercury detector 668 includes a fluidic device that can be configured to produce gas-liquid slug flow from a sample of produced gas obtained from the flow line 664 and a liquid phase reagent solution. The liquid phase reagent solution can include nanoparticles suspended in the liquid phase reagent solution. Mercury vapor of the produced gas sample is contained in the gas phase of the slug flow. The nanoparticles of the liquid phase reagent solution of the slug flow can adsorb the mercury vapor contained in the gas phase of the slug flow. The mercury detector 140 can also include an optical analyzer that performs optical analysis of the slug flow produced by the fluidic device to determine concentration of mercury in the produced gas sample.

Figure 6B:
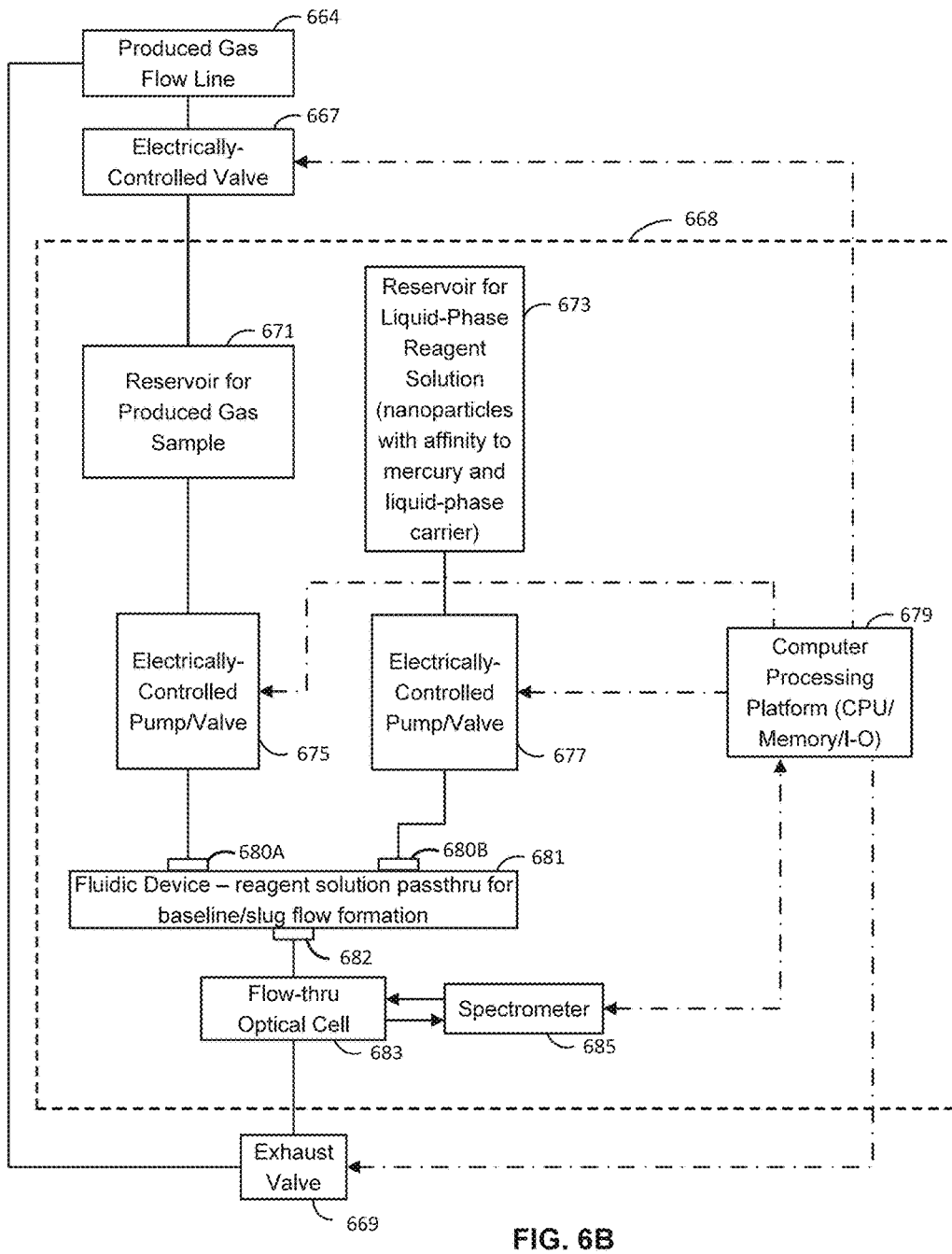
FIG. 6B is a schematic diagram showing one example of a surface-located mercury detector that can be part of the production well of FIG. 6A.

FIG. 6B depicts an illustrative embodiment of the mercury detector 668 of FIG. 6A, which performs automated fluid analysis of the produced gas sample to determine the concentration of mercury in the produced gas sample. The mercury detector 668 includes a reservoir 671 that is fluidly coupled to the gas flow line 664 via an electrically-controlled intake valve 667. The reservoir 671 can be configured to hold a produced gas sample obtained from the gas flow line 664. The produced gas sample includes gas phase hydrocarbons and possibly other gas phase components (such as mercury vapor). The mercury detector 668 also includes a reservoir 673 that is pre-loaded with a liquid phase reagent solution. The liquid phase reagent solution can include a liquid phase carrier with suspended nanoparticles that have an affinity to mercury. In some embodiments, the liquid phase reagent solution includes water as the liquid phase carrier with suspended nanoparticles of noble metal such as gold, silver, copper or be an oxide, such as zinc oxide and indium tin oxide or combinations thereof. In some embodiments, the nanoparticles can have a concentration of up to $1\times10^{15}$ nanoparticles/cm$^3$ in the liquid phase reagent solution. In some embodiments, the nanoparticles can be formed from a silica core coated with a noble metal (e.g., gold) shell, or a noble metal (e.g., gold) core coated with a silica shell, or recursive layers of silica and a noble metal (e.g., gold) possibly with varying thickness. Such nanoparticles can be designed and/or selected to have a particular SPR wavelength, which shifts due to accumulation of mercury thereon as described herein. The liquid phase reagent solution can also include a stabilizer that aids in maintaining the suspension of the nanoparticles at high temperature conditions. Note that without such a stabilizer, the high temperature conditions can destabilize the nanoparticles suspended in liquid phase reagent solution and cause precipitation. In some embodiments, the stabilizer can be a polymer soluble in the liquid phase carrier, such as poly (acrylic acid) that is water soluble for the case where water is used the liquid phase carrier.

The reservoir 671 is fluidly coupled to an electrically-controlled pump and valve 675, which are operated to pump a flow of the produced gas sample contained in the reservoir 671 to an input port 680A of the fluidic device 681. A pressure sensor (not shown) can be disposed within flow line output of the pump 675 in order to monitor the pump pressure. Such pump pressure can be can be used as a form of feedback to adjust the operation of the pump 675 in order to maintain pressure levels within the pressure rating of the apparatus 668 and to ensure that the flow of the produced gas sample into the input port 680A occurs as desired. In some embodiments, the pump and valve 675 can include an electrically-controlled syringe pump, where the syringe of the pump acts as the reservoir 671 that stores the produced gas sample.

The reservoir 673 is fluidly coupled to an electrically-controlled pump and valve 677, which are operated to pump a flow of the liquid phase reagent solution as contained in the reservoir 673 to an input port 680B of the fluidic device 681. A pressure sensor (not shown) can be disposed within flow line output of the pump 677 in order to monitor the pump pressure. Such pump pressure can be can be used as a form of feedback to adjust the operation of the pump 677 in order to maintain pressure levels within the pressure rating of the apparatus 668 and to ensure that the flow of the liquid phase reagent solution into the input port 680B occurs as desired. In some embodiments, the pump and valve 677 can include an electrically-controlled syringe pump, where the syringe of the pump acts as the reservoir 673 that stores the liquid phase reagent solution.

The fluidic device 681 produces gas-liquid slug flow from the produced gas sample introduced into the inlet port 680A and the liquid phase reagent solution introduced into the inlet port 680B. The gas phase of the slug flow is formed from the produced gas sample introduced into the inlet port 680A, and the liquid phase of the slug flow is formed from the liquid phase reagent solution introduced into the inlet port 680B. The fluidic device 681 also provides for mass transfer of any mercury vapor of the gas phase of the slug flow to the nanoparticles of the liquid phase of the slug flow to allow the mercury to absorb on the nanoparticles to form amalgam nanoparticles, which are suspended as a colloid in the liquid phase of the slug flow. The fluidic device 681 also includes an outlet port 682 that provides an outlet for the slug flow produced by the fluidic device 681. Such slug flow carries the amalgam nanoparticles as a colloid in the liquid phase of the slug flow where the degree of accumulation of mercury into the nanoparticles in the liquid phase of the slug flow is proportional to the concentration of the mercury vapor in the produced gas sample.

In some embodiments, the slug flow produced by the fluidic device 681 can be controlled by the flow rate of the produced gas sample pumped into the inlet port 680A by operation of the pump 675 and/or the flow rate of the liquid phase reagent solution pumped into the inlet port 680B by operation of the pump 677.

The outlet port 682 of the fluidic device 681 is fluidly coupled to the inlet of a flow-thru optical cell 683. A spectrometer 685 is optically coupled to the flow-thru optical cell 683 and can be configured to determine an optical spectrum of the slug flow that flows from the outlet port 682 of the fluidic device 681 and through the flow-thru optical cell 683. The slug flow that passes through the flow-thru optical cell 683 carries the amalgam nanoparticles as a colloid in the liquid phase of the slug flow where the degree of accumulation of mercury into the nanoparticles in the liquid phase of the slug flow is proportional to the concentration of the mercury vapor in the produced gas sample.

In some embodiments, the fluidic device 681 can be realized by the fluidic device shown and described above with respect to FIG. 2A, and the flow-thru optical cell 683 and spectrometer 685 can be realized by the flow-thru optical cell and spectrometer shown and described above with respect to FIGS. 2B and 2C.

An electrically-controlled exhaust valve 669 can be fluidly coupled to the outlet of the flow-thru optical cell 683 to discharge the slug flow to the flow line 664. Alternatively, the exhaust valve 669 can discharge the slug flow to a waste collection line or other suitable processing facility (not shown).

The mercury detector 668 can also include a computer processing platform 679 that interfaces to the electrically-controlled intake valve 667, the electrically-controlled pump and valve 675, the electrically-controlled pump and valve 677, the spectrometer 685, the electrically controlled exhaust valve 669 and possibly to other surface-located systems (not shown) via suitable signal paths, such as wired or wireless data connections. The computer processing platform 679 can include a CPU, computer memory (including persistent and possibly non-persistent memory) and Input-Output (or I-0) functionality that is programmed with suitable control logic to carry out a variety of functions. The control logic of the computer processing platform 679 (which can be embodied in software that is loaded from persistent memory and executed by the CPU of the computer processing platform 679) can be configured to control the different parts of the mercury detector 668 to carry out an automated sequence of operations that obtains a produced gas sample and determines the concentration of the mercury vapor in the produced gas sample. In some embodiments, the automated sequence of operations includes i) loading a sample of the produced gas into the reservoir 671, ii) pumping the produced gas sample as well as the liquid phase reagent solution held in the reservoir 673 to the fluidic device 681 to produce the slug flow, which carries the amalgam nanoparticles as a colloid in the liquid phase of the slug flow at a concentration proportional to the concentration of the mercury vapor in the produced gas sample, iii) operating the spectrometer 685 to obtain an optical spectrum of the slug flow as it flows through the optical flow-thru cell 683, and iv) operating the computer processing platform 679 to process the optical spectrum obtained by the spectrometer 685 to determine the concentration of the mercury vapor in the produced gas sample. The computer processing platform 679 can also store in computer memory data representing the concentration of the mercury vapor in the produced gas sample for output and analysis of the produced fluids.

In some embodiments, the computer processing platform 679 can process the optical spectrum obtained by the spectrometer 685 to determine a shift in the SPR peak wavelength that occurs due to a change in the permittivity of the suspended nanoparticles of the liquid phase of the slug flow as the mercury is accumulated on the nanoparticles. More specifically, as the amalgam nanoparticles form, the complex permittivity of the nanoparticles changes. This change in permittivity will change the condition for SPR coupling, which causes a spectral shift in the SPR wavelength. And the spectral shift in the SPR wavelength can be correlated to mercury concentration.

Note that control logic of the mercury detector 668 as described above can be implemented as computer program executed by the computer processing platform 679. The computer program may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processing platform. The computer instructions may be distributed in any form as a removable storage medium with accompanying printed or electronic documentation (e.g., shrink wrapped software), preloaded with a computer system (e.g., on system ROM or fixed disk), or distributed from a server over a communication system (e.g., the Internet or World Wide Web).

The computer processing platform 679 may include a CPU, other integrated circuitry (e.g., Application Specific Integrated Circuits (ASIC)), programmable logic devices (e.g., a Field Programmable Gate Arrays (FPGA) and/or discrete electronic components coupled to a printed circuit board. Any of the methods and processes described above can be implemented using such logic devices. FIG. 4 shows an example computing system 300 that can be used to implement the computer processing platform 679 as described herein. Details of the computing system 300 are described above.

Figure 7A:
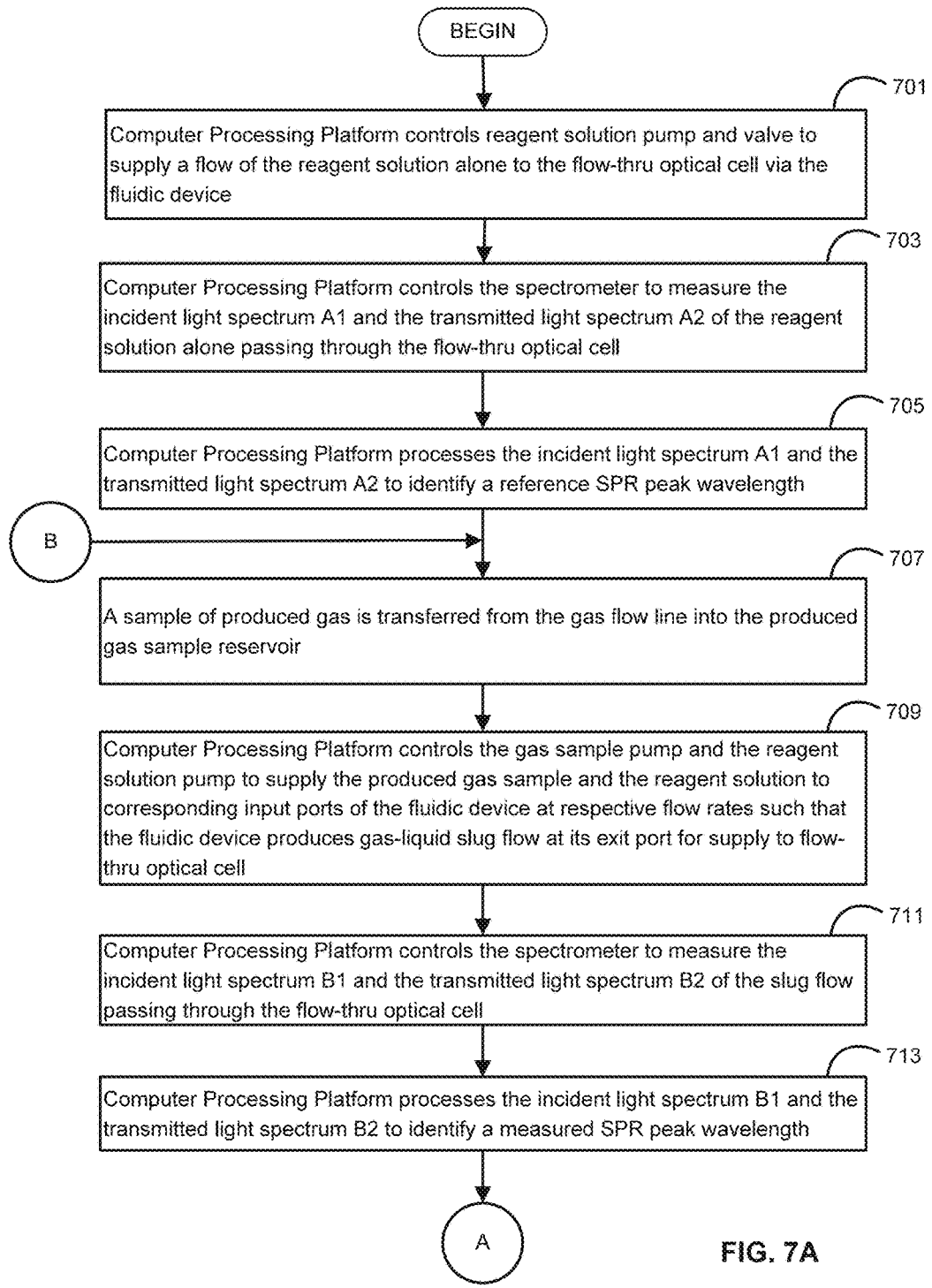
FIGS. 7A and 7B, collectively, is a flow chart illustrating an automated sequence of operations carried out by the surface-located mercury detector of FIGS. 6A and 6B according to embodiments of the present disclosure.
Figure 7B:
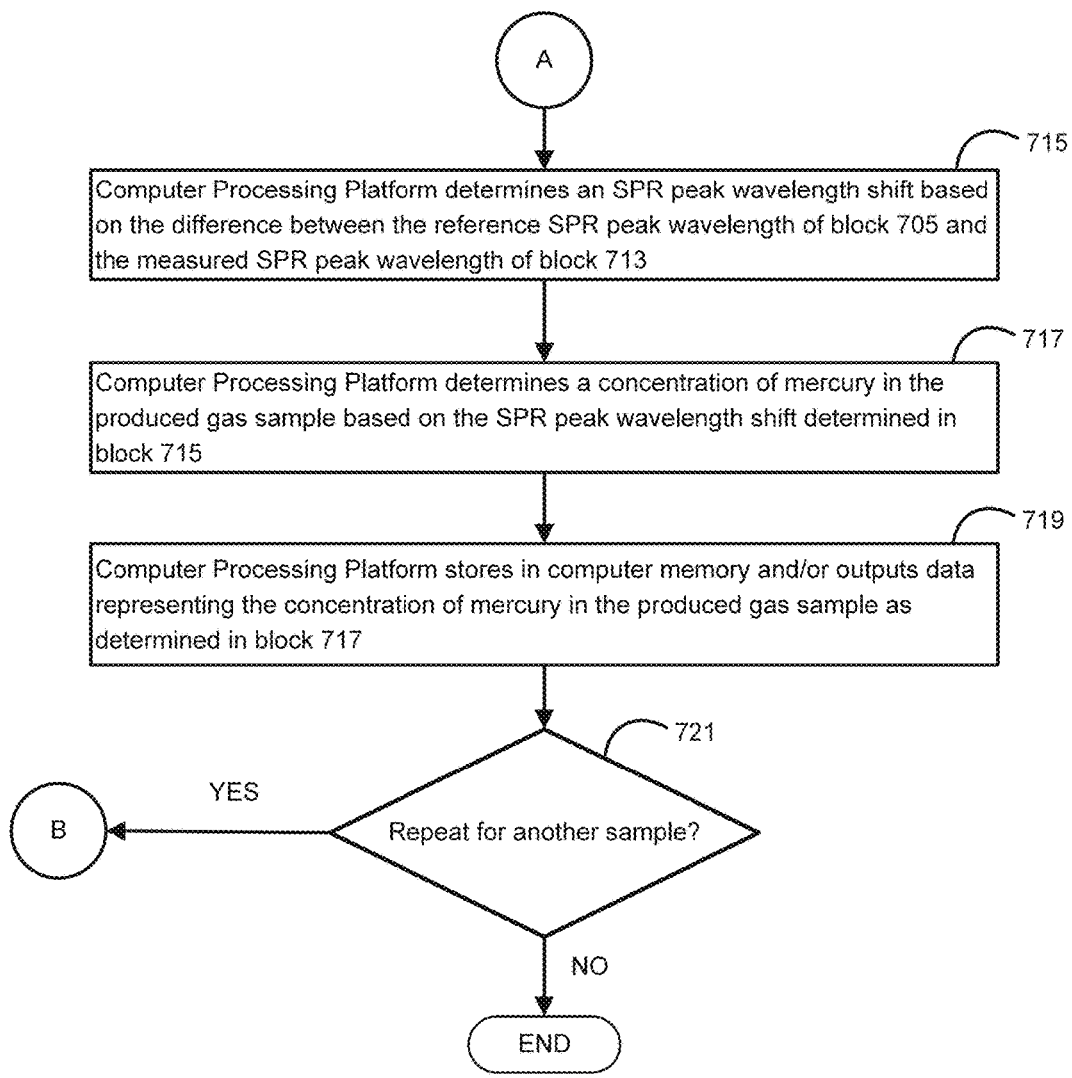

FIGS. 7A and 7B depict an automated sequence of operations carried out by the computer processing platform 679 that controls different parts of the mercury detector 140 to obtain a produced gas sample and determine the concentration of the mercury vapor in the produced gas sample. The operations begin in block 701 where the computer processing platform 679 controls the reagent solution pump and valve 677 to pump the liquid phase reagent solution held in the reservoir 673 to the input port 680B of the fluidic device 681. The computer processing platform 679 can also control the valve 675 to isolate the reservoir 671 from the input port 680A of the fluidic device 681. Such operations flow the liquid phase reagent solution alone (without any formation fluid) through the fluidic device 681 to the output port 682 for supply to the flow-thru optical cell 683, where the liquid phase reagent solution alone flows through the flow-thru optical cell 183.

In block 703, with the liquid phase reagent solution alone flowing through the flow-thru optical cell 683, the computer processing platform 679 controls the spectrometer 685 to measure the incident light spectrum A1 and the transmitted light spectrum A2 of the reagent solution passing through the flow-thru optical cell 683.

In block 705, the computer processing platform 679 processes the incident light spectrum A1 and the transmitted light spectrum A2 to identify a reference SPR peak wavelength, and stores in computer memory data representing the reference SPR peak wavelength. In some embodiments, the absorbance spectrum can be calculated as per Eqn. 1a above, where the logarithm base 10 is taken of the input intensity spectrum and divided by the transmitted intensity spectrum to yield an absorbance spectrum. The absorbance spectrum can then be analyzed with peak finding algorithms. For example, the derivative of the absorbance spectrum can be calculated. The first derivative could then be smoothed by applying a Savitzky-Golay filter with appropriate parameters. The algorithm would then look for zero-crossings in the first derivative data signifying minima and maxima on the original absorbance spectrum. The algorithm would only select downward zero-crossings (maxima on absorbance spectrum) and only take those zero-crossings where the slope exceeds a predetermined minimum called the slope threshold. At the same zero crossing, an amplitude threshold can be specified on the original absorbance spectrum to make sure the peak is of sufficient amplitude. By specifying the criteria for the smoothing filter, the slope threshold and the amplitude threshold, it is possible to identify the reference SPR wavelength. It will be appreciated that such peak finding algorithms are readily available and implemented by those skilled in the art.

In block 707, the computer processing platform 679 opens the valve 667 to transfer a produced gas sample from the gas flow line 664 into the reservoir 671.

In block 709, the computer processing platform 679 controls the produced gas pump and valve 675 and the reagent solution pump and valve 677 to supply the produced gas sample and the reagent solution to corresponding input ports 680A, 680B of the fluidic device 681 at respective flow rates such that the fluidic device 681 produces the gas-liquid slug flow at its outlet port 682 for supply to the flow-thru optical cell 683. The slug flow passes through the flow-thru optical cell 683 for analysis by the spectrometer 685. The slug flow that is produced by the fluidic device 681 and passes through the flow-thru optical cell 683 carries the amalgam nanoparticles as a colloid in the liquid phase of the slug flow where the degree of accumulation of mercury into the nanoparticles in the liquid phase of the slug flow is proportional to the concentration of the mercury vapor in the produced gas sample.

In block 711, the computer processing platform 679 controls the spectrometer to measure the incident light spectrum B1 and the transmitted light spectrum B2 of the slug flow passing through flow-thru optical cell 683.

In block 713, the computer processing platform 679 processes the incident light spectrum B1 and the transmitted light spectrum B2 to identify a measured SPR peak wavelength. Similar to the embodiment described in block 705, the absorbance spectrum can be calculated as per Eqn. 1a above, where the logarithm base 10 is taken of the input intensity spectrum and divided by the transmitted intensity spectrum to yield an absorbance spectrum. The absorbance spectrum can then be analyzed with peak finding algorithms. For example, the derivative of the absorbance spectrum can be calculated. The first derivative could then be smoothed by applying a Savitzky-Golay filter with appropriate parameters. The algorithm would then look for zero-crossings in the first derivative data signifying minima and maxima on the original absorbance spectrum. The algorithm would only select downward zero-crossings (maxima on absorbance spectrum) and only take those zero-crossings where the slope exceeds a predetermined minimum called the slope threshold. At the same zero crossing, an amplitude threshold can be specified on the original absorbance spectrum to make sure the peak is of sufficient amplitude. By specifying the criteria for the smoothing filter, the slope threshold and the amplitude threshold, it is possible to identify the measured SPR wavelength. It will be appreciated that such peak finding algorithms are readily available and implemented by those skilled in the art.

In block 715, the computer processing platform 679 determines an SPR peak wavelength shift based on the difference between the reference SPR peak wavelength of block 705 and the measured SPR peak wavelength of block 713. Note that blocks 711 to 715 can be repeated for a number of times in order to determine an effective or average SPR peak wavelength shift in block 715.

In block 717, the computer processing platform 679 determines a concentration of mercury in the produced gas sample based on the SPR peak wavelength shift determined in block 715. Such determination can be based on a correlation function of SPR peak wavelength shift to mercury concentration, for example, as shown in FIG. 3D.

In block 719, the computer processing platform 679 stores in computer memory and/or outputs data representing the concentration of mercury in the produced gas sample as determined in block 717.

In block 721, the computer processing platform 679 can determine whether to repeat the operations of block 707 to 719 for another produced gas sample. Such determination can be coordinated by operator input or determined automatically as part of an automatic test sequence. If so, the operations return to block 707 to repeat the operations of block 707 to 719 for another produced gas sample. If not, the automated sequence of operations of FIGS. 7A and 7B end.

Although only a few examples have been described in detail above, those skilled in the art will readily appreciate that many modifications are possible in the examples without materially departing from this subject disclosure.

For example, there are many variations in the mechanisms that deliver or transfer the fluids from the reservoirs to the respective input ports of the fluidic device. Examples of such method are described in U.S. Pat. No. 8,826,981, herein incorporated by reference in its entirety. For example, such methods include systems where the reagent solution is pushed in a controlled way out of the reagent reservoir and collected in a second reservoir that is pulled at such speed that a desired ratio is achieved. In another example, the fluid sample of interest can be temporarily stored in a second reservoir and then pushed in a controlled way that the optimum ratio is received. Furthermore, the reservoirs can be pressure compensated to the flow line to reduce the power needed.

Figure 8:
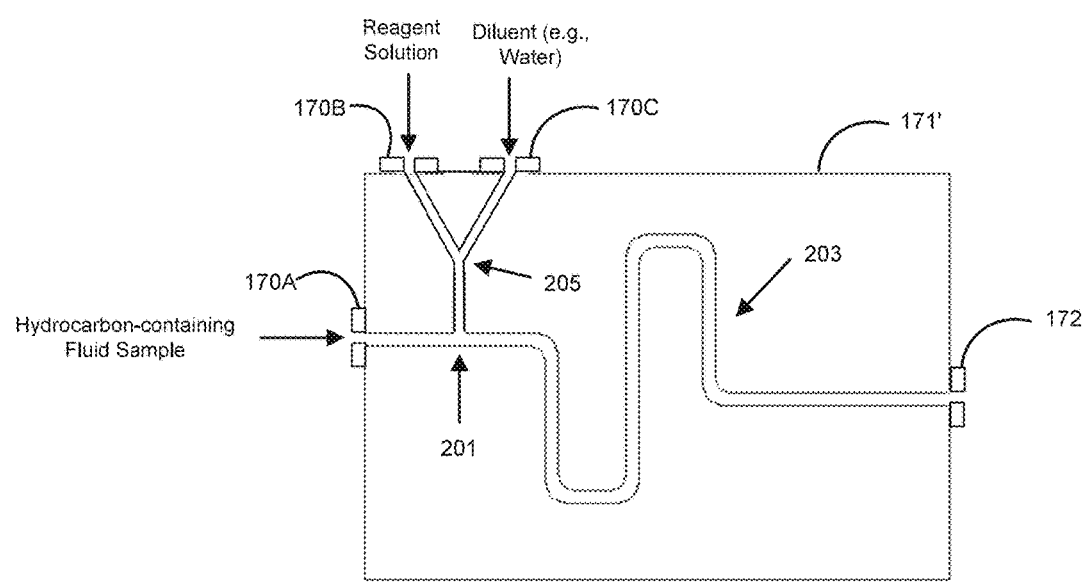
FIG. 8 is a schematic diagram showing another example of a fluidic device that can be part of the mercury detection systems of the present disclosure.

In another example, the fluidic device can provide for dilution of the reagent solution with a diluent (such as water) upstream of a mixer section that forms slug flow from the diluted reagent solution and the hydrocarbon-containing fluid sample. The dilution of the reagent solution can be controlled to attain a desired concentration range of nanoparticles in the reagent solution, which acts like "available sites" for mercury to accumulate. If there are less nanoparticles per volume, the amount of mercury accumulation per nanoparticle increases. In this way, lowering the concentration of nanoparticles in the reagent solution can amplify the extent of the SPR wavelength shift for lower concentrations of mercury. An example of such a fluidic device 171' is shown in FIG. 8, which includes an internal diluter section 205 upstream from an internal mixer section 201 and an internal reactor section 203. The diluter section 205 is a Y-type channel junction that dilutes the liquid phase reagent solution introduced into the inlet port 170B with a diluent (such as water) introduced into the inlet port 170C. The mixer section 201 is a T-type channel junction that produces a gas-liquid slug flow from the gas phase formation fluid sample introduced into the inlet port 170A and the diluted liquid phase reagent solution produced by the diluter section 205. The gas phase of the slug flow is formed from the gas phase formation fluid sample introduced into the inlet port 170A, and the liquid phase of the slug flow is formed from the diluted liquid phase reagent solution produced by the diluter section 205. The reactor section 203 is a channel that provides a flow path that allows for mass transfer of the mercury vapor of the gas phase of the slug flow to the nanoparticles of the liquid phase of the slug flow to allow the mercury to absorb on the nanoparticles to form amalgam nanoparticles. Such amalgam nanoparticles are suspended as a colloid in the liquid phase of the slug flow. The outlet port 172 at the downstream end of the flow path of the reactor section 203 provides an outlet for the slug flow produced by the fluidic device 171'. In some embodiments, the fluidic device 171' of FIG. 8 can be realized by a microfluidic device as described above. The flow rate of the diluent supplied to the inlet port 170C relative to the flow rate of the liquid phase reagent solution introduced into the inlet port 170B can be set by electronically-controlled pumps that are controlled to effect the desired dilution of the reagent solution and attain the desired concentration range of nanoparticles in the reagent solution. Such pumps can include a first pump that pumps the liquid phase reagent solution from a reservoir that holds the liquid phase reagent solution with a fixed concentration of nanoparticles for supply to the inlet port 170B and a second pump that pumps the diluent from a separate reservoir that holds the diluent for supply to the inlet port 170C. Note that the liquid phase reagent solution with the fixed concentration of nanoparticles can be supplied to the mixer section 201 in an undiluted form by operating the first pump while disabling the second pump. Also note that fluidic device of FIG. 8 can be a microfluidic device as described above.

In other examples, the fluidic device and the optical flow-thru cell can be integrated as a unitary part or package. In this configuration, the flow paths (channels) of the fluidic device and the optical flow-thru cell as described herein can possibly be integrally formed from the same glass substrate.

In still other examples, the optical analysis of the slug flow that determines mercury concentration can be based on elastic or inelastic scattering spectroscopy, reflection spectroscopy, cavity enhanced absorption spectroscopy, or other suitable spectroscopy methods.

In further examples, the fluid sampling and pumps, the fluidic device and the optical flow-thru cell of the systems and methods as described herein can be configured to obtain and process hydrocarbon fluid samples that contain oil (i.e., liquid phase sample) and/or a mixture of oil and natural gas (i.e., liquid-gas phase samples) in order to determine the mercury concentration of such fluid samples. In the case of an oil sample, the slug flow produced by the fluidic device produces a liquid-liquid (oil-reagent) slug flow with oil phase slugs and continuous phase reagent solution, where amalgam nanoparticles are carried as a colloid in the continuous phase reagent solution. In the case of an oil and natural gas sample, the slug flow produced by the fluidic device produces a gas-liquid (gas-oil/reagent) slug flow with gas phase slugs and a continuous phase which is a mixture of the oil and the reagent solution, where amalgam nanoparticles are carried as a colloid in the continuous phase mixture of the oil and the reagent solution. In both cases, the continuous phase can wet the wall(s) of the flow channel of the fluidic device, and the slugs can be separated from the wall(s) of the flow channel of the fluidic device by a thin layer of the continuous phase.

Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

As used in the description and claims, phrases in the form of "at least one of [a] and [b]" should be construed as being disjunctive, i.e., encompassing arrangements that include [a] but not [b], arrangements that include [b] but not [a], and arrangements that include [a] and [b].

What is claimed is:

1. A system for detecting mercury in hydrocarbon-containing fluid, comprising:
a first reservoir storing a sample of said hydrocarbon-containing fluid;
a second reservoir storing a liquid phase reagent solution comprising nanoparticles having an affinity to mercury suspended as a colloid in the liquid phase reagent solution;
a fluidic device having a first input port, a second input port, and a flow channel that includes a mixer section upstream from a reactor section, wherein the first input port is fluidly coupled to the first reservoir and receives a flow of the sample of the hydrocarbon-containing fluid delivered from the first reservoir, wherein the second input port is fluidly coupled to the second reservoir and receives a flow of the liquid phase reagent solution delivered from the second reservoir, wherein the mixer section is configured to produce slug flow from the hydrocarbon-containing fluid sample and the liquid phase reagent solution introduced into the first and second input ports, and wherein the reactor section is configured to extract mercury of the hydrocarbon-containing fluid sample where it adsorbs on the nanoparticles of the liquid phase reagent solution to form amalgam particles contained in slug flow that is produced by the fluidic device; and
an optical analyzer that analyzes the slug flow produced by the fluidic device and determines concentration of mercury in the sample of the hydrocarbon-containing fluid.

2. A system according to claim 1, further comprising:
a first pump configured to pump the sample hydrocarbon-containing fluid pumped from the first reservoir to the first input port of the fluidic device; and
a second pump configured to pump the liquid phase reagent solution from the second reservoir to the second input port of the fluidic device.

3. A system according to claim 1, wherein:
the liquid phase reagent solution includes water and water-soluble polymer that stabilizes the suspension of the nanoparticles in the liquid phase reagent solution at high temperature conditions.

4. A system according to claim 3, wherein:
the water-soluble polymer comprises at least one of poly(acrylic acid), poly(acrylamide-co-acrylic acid), poly(vinyl pyridine), poly(ethylene oxide), poly(vinyl alcohol), poly(4-styrene sulfonic acid), a poly (methacrylic acid), and poly (vinyl pyrrolidone).

5. A system according to claim 1, wherein:
the nanoparticles are formed from a noble metal, a silica core coated with a noble metal shell, a noble metal coated with a silica shell, or recursive layers of silica and a noble metal.

6. A system according to claim 1, wherein:
the nanoparticles have a concentration of up to $1 \times 10^{15}$ nanoparticles/$cm^3$ in the liquid phase reagent solution.

7. A system according to claim 1, wherein:
the amalgam particles are suspended as a colloid in a liquid phase of the slug flow produced by the fluidic device.

8. A system according to claim 1, wherein:
the slug flow produced by the fluidic device is controlled by the flow rate of the hydrocarbon-containing fluid sample and the flow rate of the liquid phase reagent solution supplied to the fluidic device.

9. A system according to claim 8, wherein:
the flow rate of the hydrocarbon-containing fluid sample and the flow rate of the liquid phase reagent solution supplied to the fluidic device are controlled according to fluid analysis that determines the appropriate class of fluid sample type and pump control settings that dictate the flow rate of the hydrocarbon-containing fluid sample and the flow rate of the liquid phase reagent solution for producing the desired slug flow.

10. A system according to claim 1, wherein:
the fluidic device further includes a third input port configured to receive a flow of a diluent and a diluter section upstream of the mixer section that dilutes the liquid phase reagent solution with the diluent introduced into the third input port; and the mixer section is configured to produce slug flow from the hydrocarbon-containing fluid sample introduced into the first input port and the diluted liquid phase reagent solution produced by the diluter section.

11. A system according to claim 1, wherein:
the optical analyzer includes a flow-thru optical cell, a light source, a detector, and a data processing system, wherein the light source and detector perform absorption spectroscopy that measures the transmission spectrum of light for the slug flow passing through the flow-thru optical cell, and wherein the data processing system processes the transmission spectrum to determine a shift in surface plasmon resonance (SPR) peak wavelength and uses the shift in SPR peak wavelength to determine mercury concentration in the hydrocarbon-containing fluid sample.

12. A system according to claim 1, wherein:
the hydrocarbon-containing fluid sample is selected from: a gas phase fluid sample that includes gaseous hydrocarbons, a liquid phase fluid sample that includes oil, and a gas and liquid phase fluid sample including a mixture of gaseous hydrocarbons and oil.

13. A system according to claim 1, wherein the system is part of a downhole tool configured to determine mercury concentration in a sample of formation fluid collected by the downhole tool.

14. A system according to claim 1, wherein the system is part of a surface-located facility to determine mercury concentration in fluids produced from a production well.

15. A downhole tool comprising:
a probe and flowline, wherein the probe is configured to collect formation fluid that flows into the flowline; and
the system of claim 1, fluidly coupled to the flowline, wherein the system is configured to determine mercury concentration in a sample of the formation fluid that flows into the flowline.

16. A method for detecting mercury in hydrocarbon-containing fluid, comprising:
storing a sample of the hydrocarbon-containing fluid in a first reservoir;
storing a liquid phase reagent solution in a second reservoir, wherein the liquid phase reagent solution includes nanoparticles with an affinity to mercury that are suspended as a colloid in the liquid phase reagent solution;
providing a fluidic device having a first input port, a second input port, and a flow channel that includes a mixer section upstream from a reactor section, wherein the first input port is fluidly coupled to the first reservoir, and wherein the second input port is fluidly coupled to the second reservoir;
delivering the sample of the hydrocarbon-containing fluid from the first reservoir into the first port of the fluidic device while delivering the liquid phase reagent solution from the second reservoir into the second port of the fluidic device such that the mixer section of the fluidic device produces slug flow from the hydrocarbon-containing fluid sample and the liquid phase reagent solution introduced into the first and second input ports and the reactor section of the fluidic device extracts mercury of the hydrocarbon-containing fluid sample where it adsorbs on the nanoparticles of the liquid phase reagent solution to form amalgam particles contained in slug flow that is produced by the fluidic device; and optically analyzing the slug flow produced by the fluidic device to determine concentration of mercury in the sample of the hydrocarbon-containing fluid.

17. A method according to claim 16, wherein:
the liquid phase reagent solution includes water and water-soluble polymer that stabilizes the suspension of the nanoparticles in the liquid phase reagent solution at high temperature conditions.

18. A method according to claim 17, wherein:
the water-soluble polymer comprises at least one of poly(acrylic acid), poly(acrylamide-co-acrylic acid), poly(vinyl pyridine), poly(ethylene oxide), poly(vinyl alcohol), poly(4-styrene sulfonic acid), a poly (methacrylic acid), and poly (vinyl pyrrolidone).

19. A method according to claim 16, wherein:
the nanoparticles are formed from a noble metal, a silica core coated with a noble metal shell, a noble metal coated with a silica shell, or recursive layers of silica and a noble metal.

20. A method according to claim 16, wherein:
the nanoparticles have a concentration of up to $1 \times 10^{15}$ nanoparticles/cm$^3$ in the liquid phase reagent solution.

21. A method according to claim 16, wherein:
the amalgam particles are suspended as a colloid in a liquid phase of the slug flow produced by the fluidic device.

22. A method according to claim 21, further comprising:
controlling the slug flow produced by the fluidic device by control of the flow rate of the hydrocarbon-containing fluid sample and the flow rate of the liquid phase reagent solution supplied to the fluidic device.

23. A method according to claim 22, further comprising:
controlling the flow rate of the hydrocarbon-containing fluid sample and the flow rate of the liquid phase reagent solution supplied to the fluidic device based on fluid analysis that determines the appropriate class of fluid sample type and pump control settings that dictate the flow rate of the hydrocarbon-containing fluid sample and the flow rate of the liquid phase reagent solution for producing the desired slug flow.

24. A method according to claim 16, further comprising:
delivering a diluent into a third port of the fluidic device for dilution of the liquid phase reagent solution such that the fluidic device produces slug flow from the hydrocarbon-containing fluid sample and the diluted liquid phase reagent solution.

25. A method according to claim 16, wherein:
the optical analyzing involves a flow-thru optical cell, a light source, a detector and a data processing system, wherein the light source and the detector perform absorption spectroscopy that measures the transmission spectrum of light for the slug flow passing through the flow-thru optical cell, and wherein the data processing system processes the transmission spectrum to determine a shift in surface plasmon resonance (SPR) peak wavelength and uses the shift in SPR peak wavelength to determine mercury concentration in the hydrocarbon-containing fluid sample.

26. A method according to claim 16, wherein:
the hydrocarbon-containing fluid sample is selected from: a gas phase fluid sample that includes gaseous hydrocarbons, a liquid phase fluid sample that includes oil, and a gas and liquid phase fluid sample including a mixture of gaseous hydrocarbons and oil.

27. A method according to claim 16, wherein the method is carried out by a downhole tool to determine mercury concentration in a sample of formation fluid collected by the downhole tool.

28. A method according to claim 16, wherein the method is carried out by a surface-located facility to determine mercury concentration in fluids produced from a production well.

29. A system for detecting mercury in hydrocarbon-containing fluid, comprising:
a first reservoir storing a sample of said hydrocarbon-containing fluid;
a second reservoir storing a liquid phase reagent solution comprising nanoparticles having an affinity to mercury suspended as a colloid in the liquid phase reagent solution;
a fluidic device having a first input port, a second input port, a flow channel that includes a mixer means upstream from a reactor means, the first input port being fluidly coupled to the first reservoir and receiving a flow of the sample of the hydrocarbon-containing fluid delivered from the first reservoir, the second input port being fluidly coupled to the second reservoir and receiving a flow of the liquid phase reagent solution delivered from the second reservoir, the mixer means for producing slug flow from the hydrocarbon-containing fluid sample and the liquid phase reagent solution introduced into the first and second input ports, and the reactor means for extracting mercury of the hydrocarbon-containing fluid sample where it adsorbs on the nanoparticles of the liquid phase reagent solution to form amalgam particles contained in slug flow that is produced by the fluidic device; and
an optical analyzer that analyzes the slug flow produced by the fluidic device and determines concentration of mercury in the sample of the hydrocarbon-containing fluid.

30. A system according to claim 29, wherein the mixing means comprising a junction with a plurality of inlet flow paths and an outlet flow path leading to the reactor means, wherein the plurality of inlet flow paths includes a first flow path that carries the flow of the sample of the hydrocarbon-containing fluid and a second flow path that carries the flow of the liquid phase reagent solution.

31. A system according to claim 29, wherein the reactor means comprises a flow path with a non-linear path.

32. A system according to claim 29, wherein:
the optical analyzer includes a flow-thru optical cell, a light source, a detector, and a data processing system, wherein the light source and detector perform absorption spectroscopy that measures the transmission spectrum of light for the slug flow passing through the flow-thru optical cell, and wherein the data processing system processes the transmission spectrum to determine a shift in surface plasmon resonance (SPR) peak wavelength and uses the shift in SPR peak wavelength to determine mercury concentration in the hydrocarbon-containing fluid sample.

* * * * *